US008211860B2

(12) United States Patent
Henry

(10) Patent No.: US 8,211,860 B2
(45) Date of Patent: Jul. 3, 2012

(54) CARBOHYDRATE-LIPID CONSTRUCTS AND THEIR USE IN PREVENTING OR TREATING VIRAL INFECTION

(75) Inventor: Stephen Michael Henry, Auckland (NZ)

(73) Assignee: Kode Biotech Limited, Auckland (NZ)

( * ) Notice: Subject to any disclaimer, the term of this patent is extended or adjusted under 35 U.S.C. 154(b) by 46 days.

(21) Appl. No.: 12/451,120

(22) PCT Filed: Apr. 28, 2008

(86) PCT No.: PCT/NZ2008/000095
§ 371 (c)(1),
(2), (4) Date: Mar. 29, 2010

(87) PCT Pub. No.: WO2008/133534
PCT Pub. Date: Nov. 6, 2008

(65) Prior Publication Data
US 2010/0184723 A1    Jul. 22, 2010

(30) Foreign Application Priority Data

| Apr. 27, 2007 | (NZ) | ................................ | 554853 |
| Jul. 24, 2007 | (NZ) | ................................ | 556736 |
| Apr. 24, 2008 | (NZ) | ................................ | 567754 |

(51) Int. Cl.
*A01N 43/04* (2006.01)
*A61K 31/70* (2006.01)
*C07H 17/02* (2006.01)
(52) U.S. Cl. ........................... 514/25; 536/17.9
(58) Field of Classification Search ............ 514/25
See application file for complete search history.

(56) References Cited

U.S. PATENT DOCUMENTS

| 5,451,661 | A |   | 9/1995  | Wan |           |
| 5,820,847 | A | * | 10/1998 | Low et al. ............ | 424/9.1 |
| 5,854,218 | A |   | 12/1998 | DeFrees |       |
| 7,034,006 | B2 |  | 4/2006  | Yedgar et al. |  |
| 7,101,859 | B2 |  | 9/2006  | Yedgar et al. |  |
| 2006/0189568 | A1 | | 8/2006 | Yedgar |         |
| 2007/0197466 | A1 | * | 8/2007 | Bovin et al. ............ | 514/54 |

FOREIGN PATENT DOCUMENTS

| JP | 930979 A | 7/1995 |
| JP | 2006-241095 A | 3/2005 |
| WO | WO 98/23627 A1 | 4/1998 |
| WO | WO 01/51003 A3 | 7/2001 |
| WO | WO 2005/049631 A1 | 6/2005 |
| WO | WO 2005/090368 A1 | 9/2005 |
| WO | WO 2007/035116 A1 | 3/2007 |

OTHER PUBLICATIONS

Norkin, Clinical Microbiology Reviews, Apr. 1995, p. 293-315.*
Jindrak et al. Folia Microbiol. 44(5), 467-486 (1999).*
Li, et al; "Glycerol monolaurate prevents mucosal SIV transmission"; *Nature*, vol. 458, pp. 1034-1039 (2009).
PCT International Search Report; Int'l Application No. PCT/NZ2008/000095; Int'l Filing Date Apr. 28, 2008 (4 pgs).
Asher, D.R., et al; "The erythrocyte viral trap: Transgenic expression of viral receptor on erythrocytes attenuates coxsackievirus B invection"; *PNAS*, vol. 102, No. 36; pp. 12897-12902 (2005).
Baum, J., et al; "Natural Selection on the Erythrocyte Surface"; *Mol. Biol. Evol.*, vol. 19, No. 3; pp. 223-229 (2002).
Fantini, J., et al; "Synthetic Soluble Analogs of Galactosylceramide (GalCer) Bind to the V3 Domain of HIV-1 gp120 and Inhibit HIV-1-induced Fusion and Entry"; *The Journal of Biological Chemistry*; vol. 272, No. 11; pp. 7245-7252 (1997).
Lund, N., et al; "Lack of susceptibility of cells from patients with Fabry disease to productive infection with R5 human immunodeficiency virus"; *AIDS*; vol. 19, No. 14, pp. 1543-1546 (2005).
Lund, N., et al; "A novel soluble mimic of the glycolipid, globotriaosyl ceramide inhibits HIV infection"; *AIDS*; vol. 20; pp. 333-334 (2006).
Mahfound, R., et al; "A novel soluble analog of the HIV-1 fusion cofactor, globotriaosylceramide ($Gb_3$), eliminates the cholesterol requirement for high affinity gp120/$Gb_3$ interaction"; *Journal of Lipid Research*, vol. 43, pp. 1670-1679 (2002).
Mylvaganam, M., et al; "Adamantyl Globotriaosyl Ceramide: A Monovalent Soluble Mimic Which Inhibits Verotoxin Binding to its Glycolipid Receptor"; *Biochemical and Biophysical Research Communications*; vol. 257, pp. 391-394 (1999).
Neil, S.J., et al; "HIV-1 incorporates ABO histo-blood group antigens that sensitise virions to complement-mediated inactivation"; *Blood*, prepublished online, doi:10.1182/bood-2004-11-4267, Feb. 22, 2005 (32 pgs).
Neri, P., et al; "Monovalent $Gb_3$-/$Gb_2$-Derivatives Conjugated with a Phosphatidyl Residue: A Novel Class of Shiga Toxin-Neutralizing Agent"; *Biol. Pharm. Bull*, vol. 30, No. 9, pp. 1697-1701 (2007).
Schengrund, Cara-Lynne, ""Multivalent" saccharides: development of new approaches for inhibiting the effects of glycosphingolipid-binding pathogens"; *Biochemical Pharmacology*, vol. 65, pp. 699-707 (2003).

* cited by examiner

*Primary Examiner* — Layla Bland
(74) *Attorney, Agent, or Firm* — Nixon & Vanderhye

(57) ABSTRACT

The invention relates to selected carbohydrate-lipid constructs and their use as mimics of ligands, for receptors expressed by virus. In particular, the invention relates to the use of selected carbohydrate-lipid constructs in methods of inhibiting virus infection and/or promoting clearance of virus from infected subjects. Carbohydrate-lipid constructs selected for use in these methods where the virus is Human Immunodeficiency Virus (HIV) are provided.

10 Claims, 9 Drawing Sheets

US 8,211,860 B2

CARBOHYDRATE-LIPID CONSTRUCTS AND THEIR USE IN PREVENTING OR TREATING VIRAL INFECTION

CROSS REFERENCE TO RELATED APPLICATIONS

This application is the U.S. national phase of International Application No. PCT/NZ2008/000095 filed 28 Apr. 2008 which designated the U.S. and claims priority to 554853 filed 27 Apr. 2007; 556736 filed 24 Jul. 2007, and 567754 filed 24 Apr. 2008, the entire contents of each of which are hereby incorporated by reference.

TECHNICAL FIELD

The invention relates to selected carbohydrate-lipid constructs and their use as mimics of ligands for receptors expressed by a virus.

In particular, the invention relates to the use of selected carbohydrate-lipid constructs in methods of inhibiting viral infection and/or promoting clearance of virus from infected subjects.

Carbohydrate-lipid constructs selected for use in these methods where the virus is Human Immunodeficiency Virus (HIV) are provided.

BACKGROUND ART

Infection with HIV and Acquired Immune Deficiency Syndrome (AIDS) continues to increase worldwide, despite intense research to control its spread. Furthermore, the emergence of new viral infections presents additional challenges to public health.

Therapies to treat infection that target viruses may be limited in efficacy due to resistance and genetic variance of the virus.

HIV infection is mediated by the viral fusion glycoprotein gp120-gp41 binding the cell surface expressed receptor CD4. This binding is the basis of the viral targeting of T lymphocytes and monocyte macrophages. The receptor gp120 shows an affinity in vitro for several glycosphingolipids (GSLs) (Bhat at al (1993); Fantini at al (1998); Mylvaganam and Lingwood (1999a)).

A need exists for glycolipid mimics that are dispersible in biocompatible media and can be used to modify the interaction between naturally occurring membrane incorporated glycoconjugates, such as GSLs, and the receptors expressed by a virus. Such water soluble glycolipid mimics have been recognized as having potential for use in the preventative treatment of individuals at risk of infection from viruses such as HIV.

Lund et al (2006) have investigated the effect of the water soluble glycolipid mimic adamantylGb$_3$ on HIV infection of cells in culture. In previous studies adamantylGb$_3$ had been demonstrated to be a superior ligand for the receptor gp120 (Mahfoud at al (2002)).

A dose dependent inhibition of infection of Jurkat T cells by HIV-1 pre-incubated with adamantylGb$_3$ has been demonstrated in vitro (Lund et al 2006). The in vivo inhibition of infection by HIV-1 was not reported, but the water soluble glycolipid mimic was indicated to have no effect on Jurkat T cell viability. Transient changes in CD4 surface expression were observed. Lund et al (2006) attributed the dose dependent inhibition of infection to an inhibition of attachment of the pre-treated HIV-1 to the Jurkat T cells. The adamantylGb$_3$ treated virus remained non-host cell attached and virions could not be found within the Jurkat cells.

Further studies on HIV-1 infection of primary lymphoid cells in vitro provided results consistent with those observed for Jurkat T cells as host cells. Infection by both wild type and drug resistant HIV-1 infection was inhibited by the pre-treatment of the water soluble glycolipid mimic adamantylGb$_3$. However, pre-incubation of cells with adamantylGb$_3$ was ineffective.

Lund et al (2006) noted the effective concentration range required to inhibit HIV-1 infection would be difficult to maintain clinically, but suggested the formulation of adamantylGb$_3$ within a cream might provide a topical ointment for the prevention of mucosal HIV infection.

It is an object of the invention to provide receptor binding carbohydrate-lipid constructs that are effective to inhibit viral infection of the cells of a subject.

It is a further object of the invention to provide receptor binding carbohydrate-lipid constructs that are effective to promote clearance of virus from an infected subject.

These objects are to be read disjunctively with the object of to at least provide a useful choice.

DISCLOSURE OF INVENTION

In a first aspect the invention provides a method of inhibiting infection of the cells of a subject by a virus by administering to the subject an amount of carbohydrate-lipid construct of the formula F-S$_1$-S$_2$-L where:
  F is selected from the group consisting of glycotopes of ligands for one or more receptors expressed by the virus;
  S$_1$-S$_2$ is a spacer linking F to L; and
  L is a lipid selected from the group consisting of diacyl- and dialkyl-glycerolipids, including glycerophospholipids.

Preferably, the amount is effective to inhibit binding of the receptor expressed by the virus to a cell surface expressed ligand.

Preferably, the receptor is expressed by the human immunodeficiency virus (HIV).

S$_1$-S$_2$ is selected to provide a carbohydrate-lipid construct that is dispersible in water.

Preferably, S$_1$ is a C$_{2-5}$-aminoalkyl selected from the group consisting of: 2-aminoethyl; 3-aminopropyl; 4-aminobutyl; and 5-aminopentyl.

Preferably, S$_2$ is selected from the group consisting of: —CO(CH$_2$)$_3$CO—; —CO(CH$_2$)$_4$CO— (adipate); and —CO(CH$_2$)$_5$CO—.

Preferably, L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably, the lipid is derived from one or more cis-desaturated fatty acids. Most preferably, L is selected from the group consisting of: 1,2-O-dioleoyl-sn-glycero-3-phosphatidylethanolamine (DOPE) and 1,2-O-distearyl-sn-glycero-3-phosphatidylethanolamine (DSPE); and rac-1,2-dioleoylglycerol (DOG).

Preferably, L is a glycerophospholipid and the construct includes the substructure:

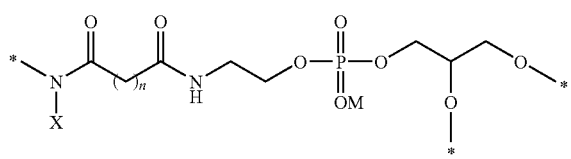

where X is H or C, * is other than H and n is an integer 2 to 5.
More preferably, L is a glycerophospholipid and the construct includes the substructure:

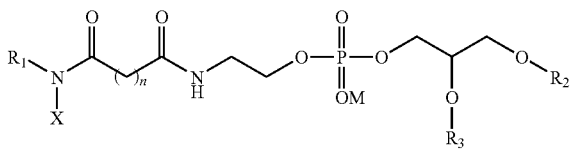

where:

X is H;

$R_1$ is a $C_p$-alkyl glycoside, $R_2$ and $R_3$ are independently selected from the group consisting of: trans-3-hexadecenal, cis-5-hexadecenal, cis-7-hexadecenal, cis-9-hexadecenal, cis-6-octadecenal, cis-9-octadecenal, trans-9-octadecenal, trans-11-octadecenal, cis-11-octadecenal, cis-11-eicosenal and cis-13-docsenal;

n is 2 to 5; and p is 2 or 3.

Most preferably, the glycoside is 1-O—(O-α-D-galactopyranosyl-(1→4)-O-β-D-galactopyranosyl-(1→4)-β-D-glucopyranosyl ($Gb_3$), n is 4 and p is 3.

In specific embodiments of the first aspect of the invention the carbohydrate-lipid construct has the structure:

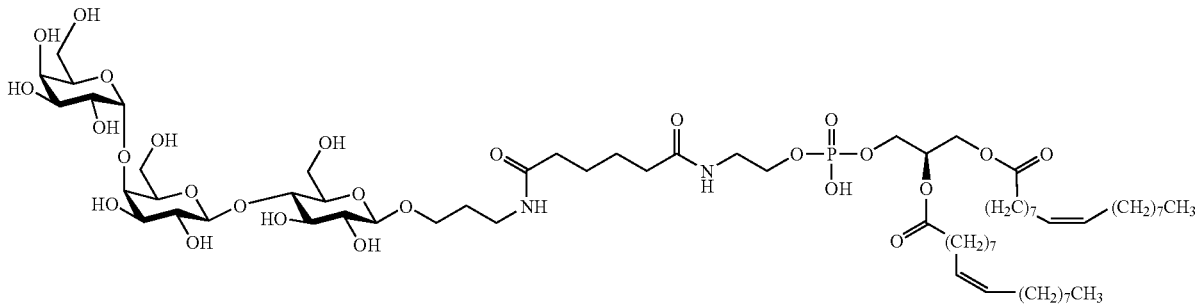

designated $Gb_3$-sp3-Ad-DOPE (I); the structure:

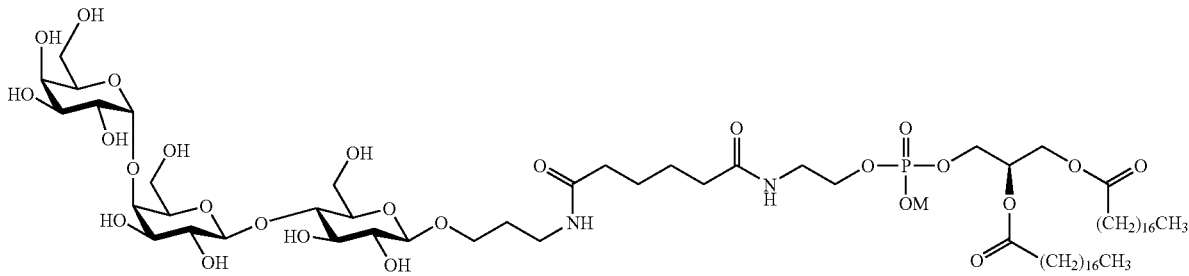

designated $Gb_3$-sp3-Ad-DSPE (II); the structure:

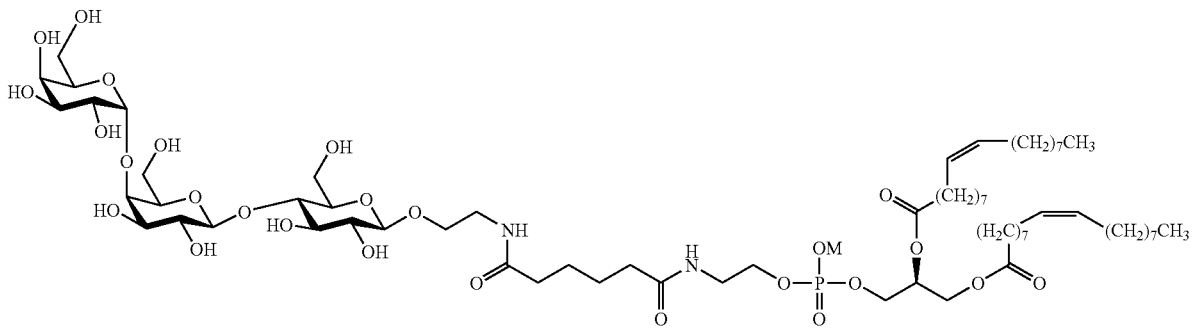

designated Gb₃-sp2-Ad-DOPE (III); or the structure:

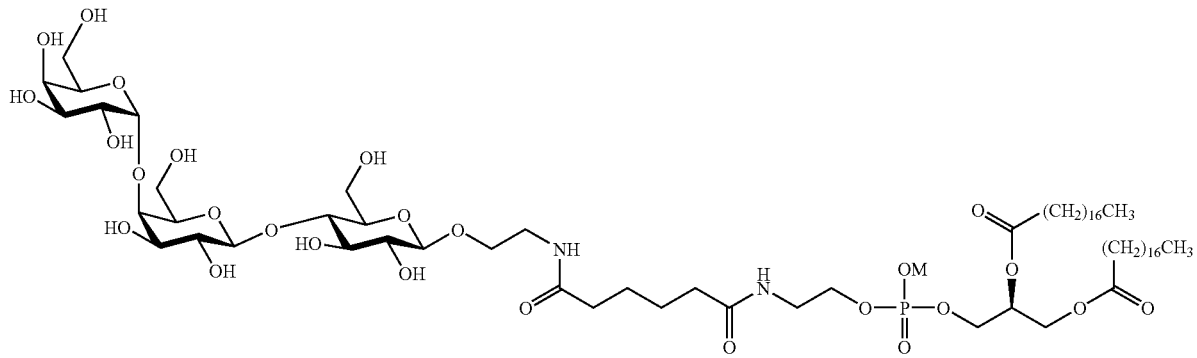

designated Gb₃-sp2-Ad-DSPE (IV).

In a first embodiment of the first aspect of the invention the administering to the subject is by intravascular injection. Preferably, the administering is by intravenous injection. Preferably, the administering to the subject is to provide a concentration in the plasma of the subject of greater than 400 μM.

In a second embodiment of the first aspect of the invention the administering to the subject is by topical application. Preferably, the administering to the subject is by topical application as a cream or suppository.

In a second aspect the invention provides a method of promoting clearance of a virus from an infected subject by administering to the subject an amount of carbohydrate-lipid construct of the formula F-S₁-S₂-L where:
  F is selected from the group consisting of glycotopes of ligands for one or more receptors expressed by the virus;
  S₁-S₂ is a spacer linking F to L; and
  L is a lipid selected from the group consisting of diacyl- and dialkyl-glycerolipids, including glycerophospholipids.

Preferably, the administering to the subject is by intravascular injection. More preferably, the administering is by intravenous injection.

Preferably, the amount is sufficient to promote partitioning of the carbohydrate-lipid construct into the membranes of cells of the vascular system.

Preferably, the administering to the subject is to provide an initial concentration in the plasma of the subject of greater than 400 μM.

Preferably, the receptor is expressed by the human immunodeficiency virus (HIV).

S₁-S₂ is selected to provide a carbohydrate-lipid construct that is dispersible in water:

Preferably, S₁-S₂ is selected to provide a carbohydrate-lipid construct that partitions into a lipid bi-layer when a solution of the construct is contacted with the lipid bi-layer.

Preferably, S₁ is a C₂₋₅-aminoalkyl selected from the group consisting of: 2-aminoethyl, 3-aminopropyl, 4-aminobutyl, or 5-aminopentyl.

Preferably, S₂ is selected from the group consisting of: —CO(CH₂)₃CO—, —CO(CH₂)₄CO-(adipate), —CO(CH₂)₅CO— and —CO(CH₂)₅NHCO(CH₂)₅CO—.

Preferably, L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably, the lipid is derived from one or more cis-desaturated fatty acids. Most preferably, L is selected from the group consisting of: 1,2-O-dioleoyl-sn-glycero-3-phosphatidylethanolamine (DOPE) and 1,2-O-distearyl-sn-glycero-3-phosphatidylethanolamine (DSPE); and rac-1,2-dioleoylglycerol (DOG).

Preferably, L is a glycerophospholipid and the construct includes the substructure:

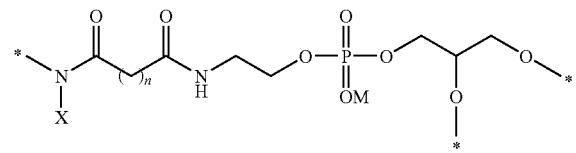

where X is H or C, * is other than H and n is an integer 2 to 5.

More preferably, L is a glycerophospholipid and the construct includes the substructure:

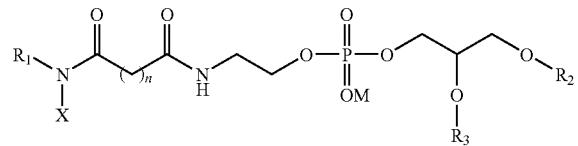

where:
  X is H;
  R₁ is a C_p-alkyl glycoside,
  R₂ and R₃ are independently selected from the group consisting of: trans-3-hexadecenal, cis-5-hexadecenal, cis-7-hexadecenal, cis-9-hexadecenal, cis-6-octadecenal, cis-9-octadecenal, trans-9-octadecenal, trans-11-octadecenal, cis-11-octadecenal, cis-11-eicosenal or cis-13-docsenal;
  n is 2 to 5; and
  p is 2 or 3.

Most preferably, the glycoside is 1-O—(O-α-D-galactopyranosyl-(1→4)-O-β-D-galactopyranosyl-(1→4)-β-D-glucopyranosyl (Gb₃), n is 4 and p is 3.-

In specific embodiments of the second aspect of the invention the carbohydrate-lipid construct has the structure:
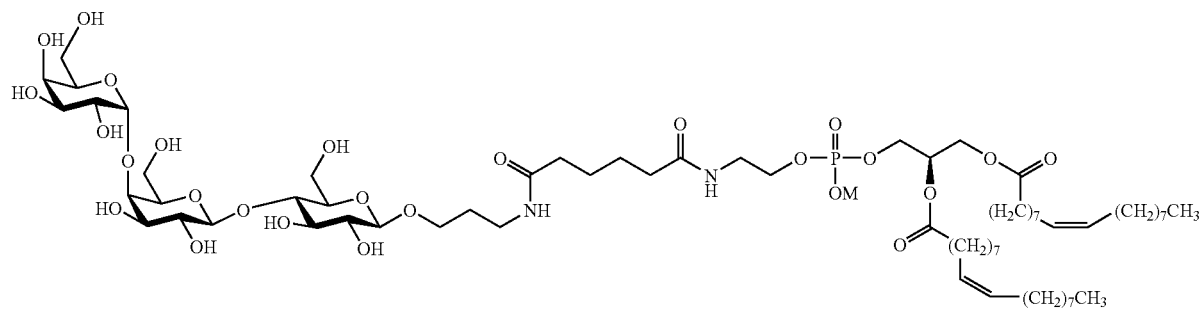
designated Gb$_3$-sp3-Ad-DOPE (I); the structure:
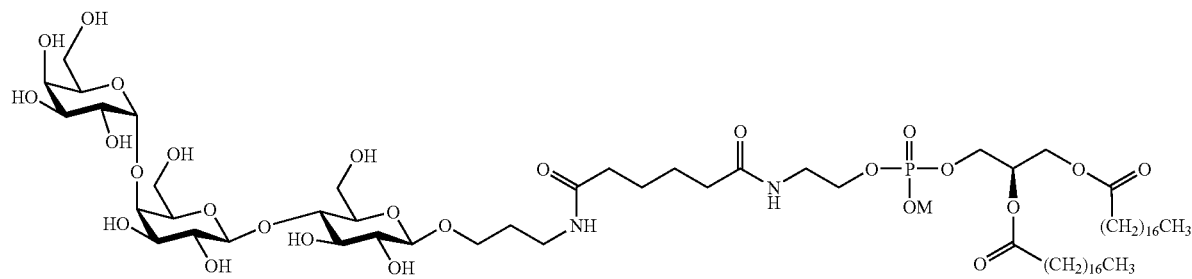
designated Gb$_3$-sp3-Ad-DSPE (II); the structure:
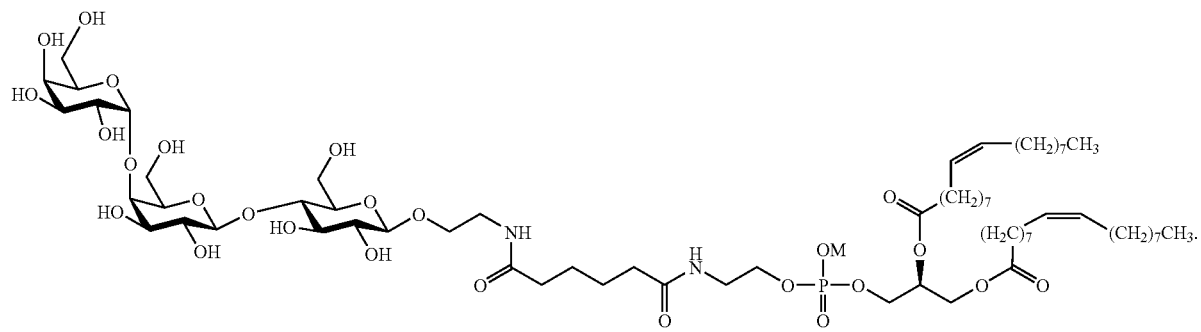
designated Gb$_3$-sp2-Ad-DOPE (III); or the structure:
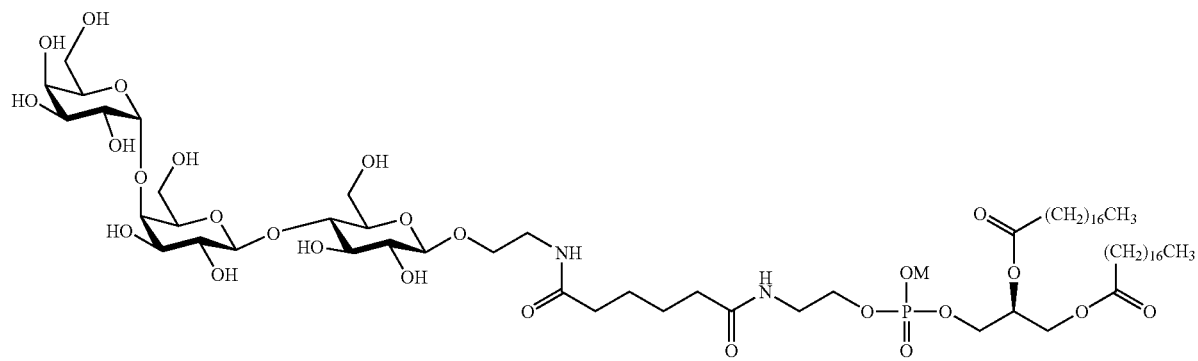
designated Gb$_3$-sp2-Ad-DSPE (IV).

In a third aspect the invention provides a pharmaceutical preparation for administration to a subject comprising a receptor binding carbohydrate-lipid construct of the formula F-$S_1$-$S_2$-L where:

F is selected from the group consisting of glycotopes of ligands for a receptor;
$S_1$-$S_2$ is a spacer linking F to L; and
L is a lipid selected from the group consisting of diacyl- and dialkyl-glycerolipids, including glycerophospholipids; and
pharmaceutically acceptable formulants.

Preferably, the receptor is expressed by a virus. More preferably, the receptor is expressed by the human immunodeficiency virus (HIV).

Preferably, the pharmaceutical preparation is in the form of a cream or suppository.

$S_1$-$S_2$ is selected to provide a carbohydrate-lipid construct that is dispersible in water.

Preferably, $S_1$-$S_2$ is selected to provide a carbohydrate-lipid construct that partitions into a lipid bi-layer when a solution of the construct is contacted with the lipid bi-layer.

Preferably, $S_1$ is a $C_{2-5}$-aminoalkyl selected from the group consisting of: 2-aminoethyl, 3-aminopropyl, 4-aminobutyl, or 5-aminopentyl.

Preferably, $S_2$ is selected from the group consisting of: —CO(CH$_2$)$_3$CO—; —CO(CH$_2$)$_4$CO-(adipate); and —CO(CH$_2$)$_5$CO—.

Preferably, L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably, the lipid is derived from one or more cis-desaturated fatty acids. Most preferably, L is selected from the group consisting of: 1,2-O-dioleoyl-sn-glycero-3-phosphatidylethanolamine (DOPE) and 1,2-O-distearyl-sn-glycero-3-phosphatidylethanolamine (DSPE); and rac-1,2-dioleoylglycerol (DOG).

Preferably, L is a glycerophospholipid and the construct includes the substructure:

where X is H or C, * is other than H and n is an integer 2 to 5.

More preferably, L is a glycerophospholipid and the construct includes the substructure:

where:
X is H;
$R_1$ is a $C_p$-alkyl glycoside,
$R_2$ and $R_3$ are independently selected from the group consisting of: trans-3-hexadecenal, cis-5-hexadecenal, cis-7-hexadecenal, cis-9-hexadecenal, cis-6-octadecenal, cis-9-octadecenal, trans-9-octadecenal, trans-11-octadecenal, cis-11-octadecenal, cis-11-eicosenal or cis-13-docsenal;
n is 2 to 5; and
p is 2 or 3.

Most preferably, the glycoside is 1-O—(O-α-D-galactopyranosyl-(1→4)-O-β-D-galactopyranosyl-(1→4)-β-D-glucopyranosyl (Gb$_3$), n is 4 and p is 3.

In specific embodiments of the third aspect of the invention the carbohydrate-lipid construct has the structure:

designated Gb$_3$-sp3-Ad-DOPE (I); the structure:

designated Gb$_3$-sp3-Ad-DSPE (II); the structure:

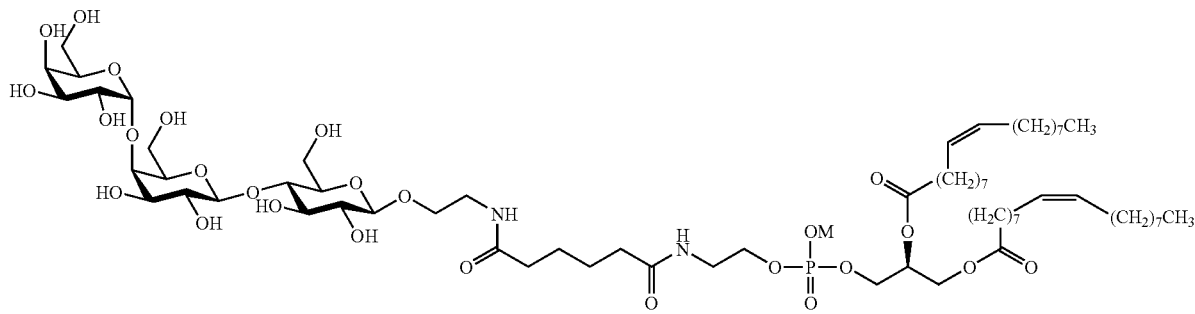

designated Gb$_3$-sp2-Ad-DOPE (III); or the structure:

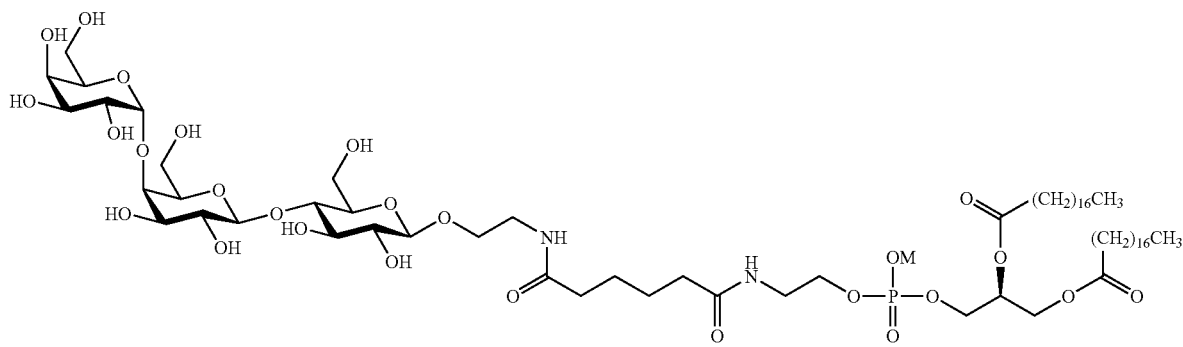

designated Gb$_3$-sp2-Ad-DSPE (IV).

In a first embodiment of the third aspect of the invention the pharmaceutical preparation is formulated for administration by intravascular injection. Preferably, the pharmaceutical preparation is formulated for administration by intravenous injection. More preferably, the pharmaceutical preparation is formulated as an aqueous formulation. Yet more preferably, the pharmaceutical preparation is a suspension of red blood cells of the subject modified to incorporate the receptor binding carbohydrate-lipid construct. Most preferably, the pharmaceutical preparation is identified for use in inhibiting HIV infection and/or promoting clearance of HIV from infected subjects.

In a third embodiment of the third aspect of the invention the pharmaceutical preparation is formulated for administration as a cream or suppository. Preferably, the pharmaceutical preparation is formulated for administration as a cream. More preferably, the pharmaceutical preparation is formulated as an aqueous formulation. Most preferably, the pharmaceutical preparation is identified for use in inhibiting or preventing HIV infection.

In the description and claims of the specification the following terms and phrases have the meaning provided:

"Carbohydrate-lipid construct" means a synthetic molecule used as a glycolipid mimic.

"Gb3" means the carbohydrate portion of the ganglioside Gb3 (Chemical Abstract Service (CAS) REGISTRY number 71965-57-6)

"C$_p$-alkyl glycoside" means an alkyl glycoside consisting of an unbranched chain of p methylene units attached to the carbohydrate via a glycosidic linkage as exemplified by the propyl glycoside (p is 3) of the structure:

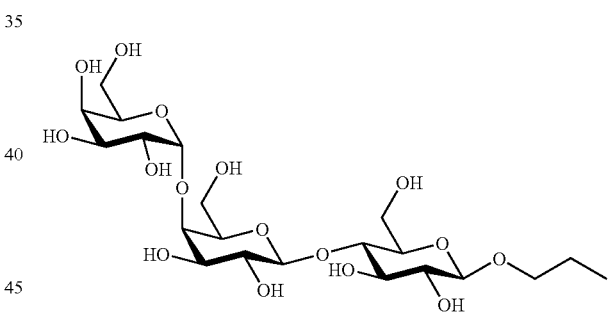

designated Gb$_3$-sp3.

"Dispersible in water" means a stable, single phase dispersion of the carbohydrate-lipid construct may be prepared in water at a concentration of up to at least 1000 μM in the absence of organic solvents or detergents.

"Glycotope" means the portion of the carbohydrate moiety of a ligand that associates with the binding site of a receptor.

"Ligand" means any molecule or portion of a molecule that binds to one or more macromolecules, such as surface expressed antigens.

"Pharmaceutically acceptable formulants" means ingredients included in the formulation of a pharmaceutical composition.

"Receptor" means a macromolecule or portion of a macromolecule such as a surface expressed antigen that binds to one or more ligands.

"Vascular system" means the system of vessels that convey fluids such as blood or lymph, or provide for the circulation of such fluids.

In the context of administering to the subject to provide a specified concentration in the plasma of the subject the administering may be by repeated administration to maintain the specified concentration in the plasma.

From the structures and substructures of the carbohydrate-lipid constructs it will be recognised that M is typically H, but may be replaced by another monovalent cation such as $Na^+$, $K^+$, $NH_4^+$ and triethylamine ($[NH(CH_2CH_3)_3]^+$), and the secondary amino functions of the carbohydrate-lipid construct may be protonated. The carbohydrate-lipid constructs may be prepared as a range of pharmaceutically acceptable salts.

Where the suffix "-al" is employed in respect of the substituents $R_2$ and $R_3$, an aldehyde structure is intended as exemplified by cis-9-octadecenal of the structure:

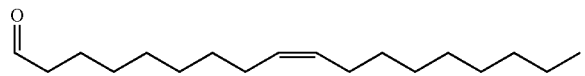

The invention will now be described in detail with reference to examples and the Figures of the accompanying drawings pages that are indicative of the utility of the subject matter claimed in the treatment of human subjects.

DETAILED DESCRIPTION

Figure 1:
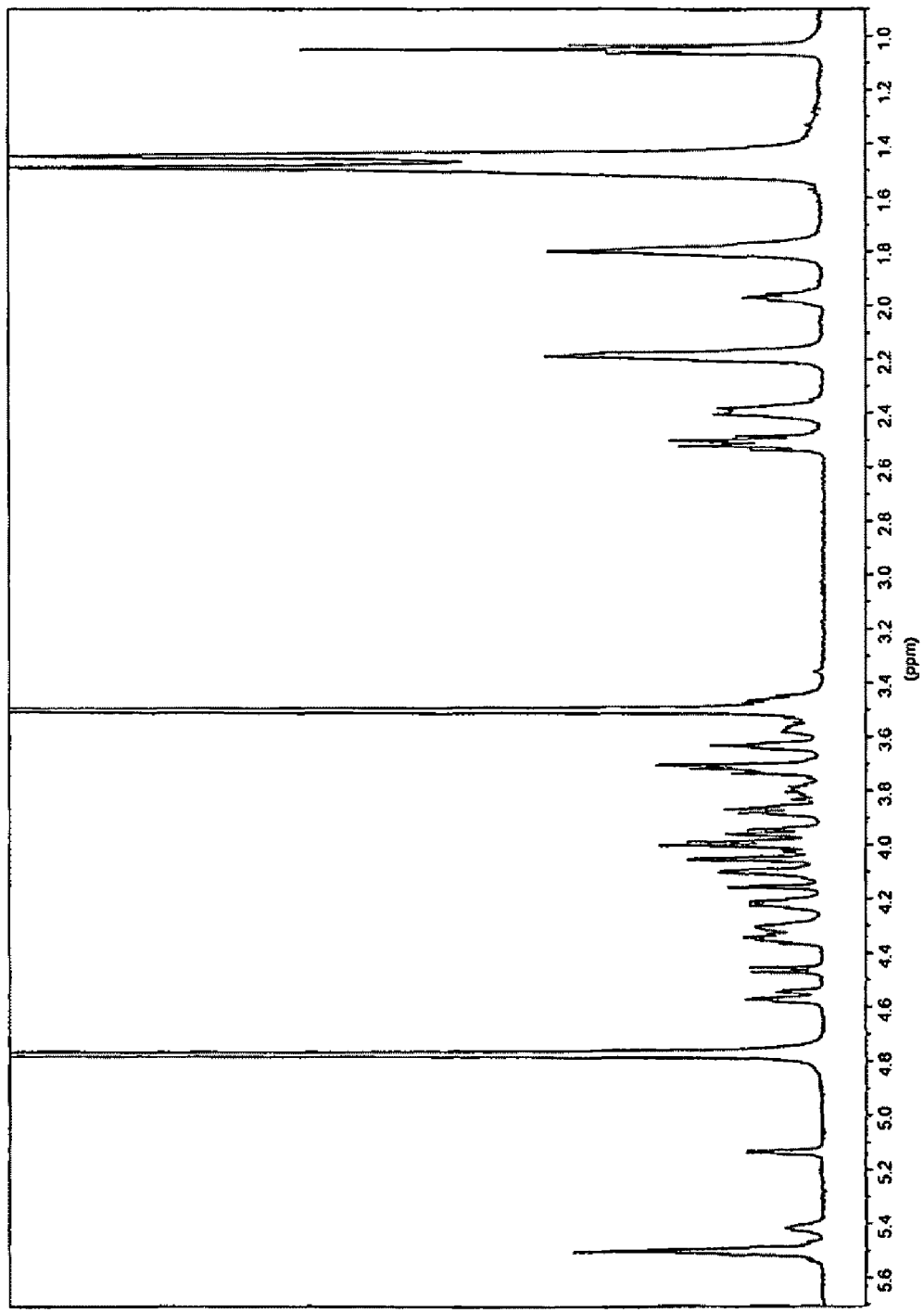
FIG. 1. $^1$H-NMR data for the carbohydrate-lipid construct designated Gb$_3$-sp3-Ad-DOPE (I).

The specification accompanying international application no. PCT/NZ2005/000052 (publication no. WO 2005/090368) describes the preparation and use of water soluble carbohydrate-lipid constructs. In one example of the use of these constructs, qualitative and quantitative changes in the surface antigen expression of red blood cells (RBCs) is effected to provide quality control cells (e.g. SECURACELL™) for use in validation of blood grouping.

Naturally occurring glycoconjugates, such as GSLs are not readily dispersible in water. Furthermore, it has been recognized that isolated GSLs do not always retain the binding characteristics of the membrane-bound glycolipid. In fact it is stated in the specification accompanying international application no. PCT/CA97/00877 (publication no. WO 98/23627) that solubilised GSLs may have little or no binding affinity for compounds which bind strongly to the membrane bound GSL.

Mylvaganam and Lingwood (1999d) stated in the context of binding between the GSL globotriaosyl ceramide (Gb$_3$) and the bacterial toxin verotoxin that the reduction in binding affinity may be attributed to conformational changes influenced by the aglycone moiety. When incorporated in the plasma membrane conformational changes (favourable orientations) of the glycone moiety may be restricted by the plane of the membrane. The development of water soluble glycolipid mimics was pursued resulting in adamantyl conjugates which retained affinity for the verotoxin receptor.

The carbohydrate-lipid constructs described in the specification accompanying international application no. PCT/NZ2005/000052 are dispersible in water and spontaneously incorporate into cell membranes as demonstrated by their use in the preparation of quality control cells.

The present invention provides selected carbohydrate-lipid constructs that are glycolipid mimics, but are dispersible in aqueous or biocompatible media. The constructs may therefore be used in methods of preventing infection of cells by viruses in vivo.

The selected carbohydrate-lipid constructs are of the general formula F-S$_1$-S$_2$-L where the alkylglycoside portion (F-S$_1$) is selected to provide a ligand for a receptor expressed by a virus, and the spacer portion (S$_1$-S$_2$) is selected to provide a dispersible construct.

The constructs may function to inhibit both:
1. natural ligand-receptor binding (including "multivalent" binding (Schengrund (2003)); and
2. post-binding events essential to infection of the target host cell and subsequent replication of the virus.

As noted by Lund et al (2006) HIV targeting of CD4 and chemokine co-receptor expressing lymphoid and monocytic cells has long been appreciated as the major mechanism of HIV-host cell interaction.

The gp120 receptor has also been shown to have an affinity in vitro for a number of GSLs including galactosyl ceramide, sulphogalactosyl ceramide and GM3 ganglioside (Feng et al (1996); Bhat et al (1993); Fantini et al (1998)). This binding affinity is characterized at least in part by the nature of the carbohydrate moiety (glycotope) of the GSL ligand. The receptor-GSL binding facilitates a post-CD4 binding event to allow the host cell entry of diverse HIV strains (Nehete et al (2002)).

Whilst not wishing to be bound by theory it is believed that inhibiting the receptor-GSL binding event with a water soluble carbohydrate-lipid construct will inhibit host cell entry and viral infection of the cells. Furthermore, it is believed that inhibiting the post-CD4 binding event in situ, i.e. at the co-receptor expressing surface of lymphoid and monocytic cells will promote clearance of virus from an infected subject.

The in situ inhibition of the post-CD4 binding event may occur when the water soluble carbohydrate-lipid construct is incorporated into the cell membrane of the lymphoid and monocytic cells. The formation of carbohydrate-lipid construct enriched lipid microdomains on the host cell surface may be central to both inhibiting viral infection and promoting clearance of virus from an infected subject.

The methods of the invention may be effective against a plurality of types of HIV, including types X4 and R5. The ability of the carbohydrate-lipid constructs to inhibit infection of cells by type R5 HIV-1 is of particular significance as this is a strain of virus that initially infects susceptible subjects.

The carbohydrate-lipid constructs selected for use in the methods of the invention are water soluble constructs that will partition, i.e. incorporate, into cell membranes. Furthermore, the preparation of these synthetic constructs excludes the use of substrates or reagents derived from zoological sources. The carbohydrate-lipid constructs therefore provide advantages over semi-synthetic water soluble glycolipid mimics such as the adamantylGb$_3$ conjugates.

A number of receptor binding carbohydrate-lipid constructs may be effective to inhibit infection or promote clearance of virus from infected subjects. In addition to carbohydrate-lipid constructs including a Gb$_3$ carbohydrate moiety, constructs including the glycotope of the GM3 carbohydrate moiety may also prove effective inhibitors of HIV infection and promote clearance of the virus from an infected subject. Methods comprising the administration of two or more water soluble carbohydrate-lipid constructs are contemplated.

The use of the carbohydrate-lipid constructs in the methods of the invention is believed to be particularly advantageous because of the ability of the constructs to incorporate non-specifically into the membranes of cells in vivo. The non-specific modification of cells in vivo may permit multivalent binding and the adherence of the virus to cells in which the virus is unable to replicate.

Adherence to the cell surface of a cell via the carbohydrate portion of the carbohydrate-lipid construct may also result in the virus being trapped at the cell surface (cf. Asher et al (2005)). The ability of the immune system to recognise and respond to the presence of virus may therefore be augmented.

Although discussed with reference to the prevention and treatment of subjects with HIV infection, it will be recognised that a number of viral infections are initiated by the adherence of the virus to carbohydrates expressed at the surface of cells.

Schengrund (2003) and others have reviewed the development of saccharides as pharmacologic agents. As noted by this author, where it is determined that the expression of glycosphingolipids is necessary for infection (Fantini et al (1993); Hanada (2005); Karlsson (1995); Is a et al (1997); Matrosovicha et al (1997); Miller-Podraza et al (2000); Suzuki (1994); Connor et al (1994); Matrpsovich at al (1999); Willoughby at al (1990)), the opportunity arises to interfere with the adherence of the virus (e.g. influenza virus, rotavirus) to the surface of target cells.

Experimental

The carbohydrate-lipid constructs designated Gb$_3$-sp3-Ad-DOPE (I) and Gb$_3$-sp2-Ad-DOPE (III) may be prepared and characterized in accordance with the methods described mutatis mutandis in the specification accompanying international application number PCT/NZ2005/000052 (publication no. WO 2005/090368) and summarized in Schemes I, II and IV.

The carbohydrate-lipid construct designated Gb$_3$-sp2-Ad-DOPE (III) may also be prepared by the method described below and summarized in Schemes III and IV.

Scheme I: (a) Cl$_3$CNN, DBU, CH$_2$Cl$_2$, −5° C., 64%; (b) Cl(CH$_2$)$_3$OH, BF$_3$*Et$_2$O, MS-4A, CH$_2$Cl$_2$, −5° C., 65%; (c) NaN$_3$, DSMO, 80° C., 20 h, 91%; (d) i) NaOMe/MeOH, 80%, ii) DMT, p-TsOH, DMF, 63%; (e) NaH, BnBr, 0° C., DMF, 87%; (f) NaCNBH$_3$, HCl*Et$_2$O, MS-3A, −5° C., THF, 73%; (g) i) PPh$_3$, H$_2$O, THF, ii) MeOCOCF$_3$, Et$_3$N, THF, 84%

Scheme II: (a) Cl$_3$CNN, K$_2$CO$_3$, CH$_2$Cl$_2$, 60%; (b) TMSOTf, MS-4A, CH$_2$Cl$_2$, 72% (c) H$_2$, 10% Pd/C, MeOH; (d) Ac$_2$O/Py, 90% (e) MeONa/MeOH (f) NaOH/H$_2$O, 96%

Scheme III: (a) Br$_2$, CH$_2$Cl$_2$, +4° C., 100%; (b) AgOTf, MS-4A, CH$_2$Cl$_2$, 78%; (c) MeONa/MeOH—CH$_2$Cl$_2$; (d) H$_2$, 10% Pd/C, MeOH, Boc$_2$O, 70%; (e) CF$_3$COOH (95%), 96%

Scheme IV: (a), (b) DMF/CH$_2$Cl$_2$, Et$_3$N, 90-95%

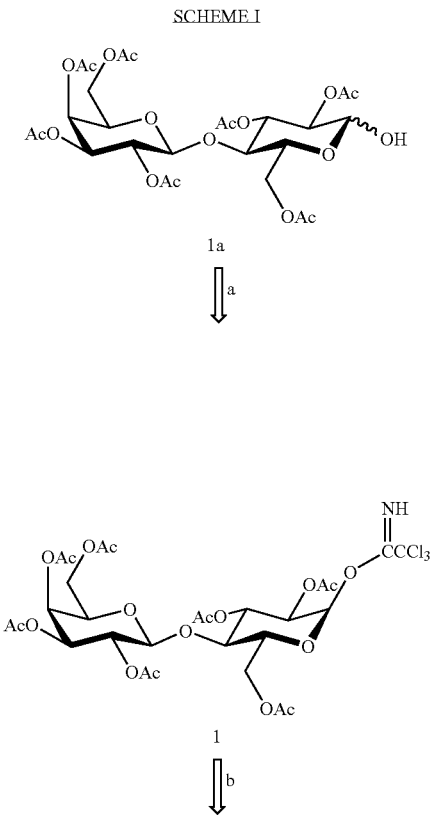

SCHEME I

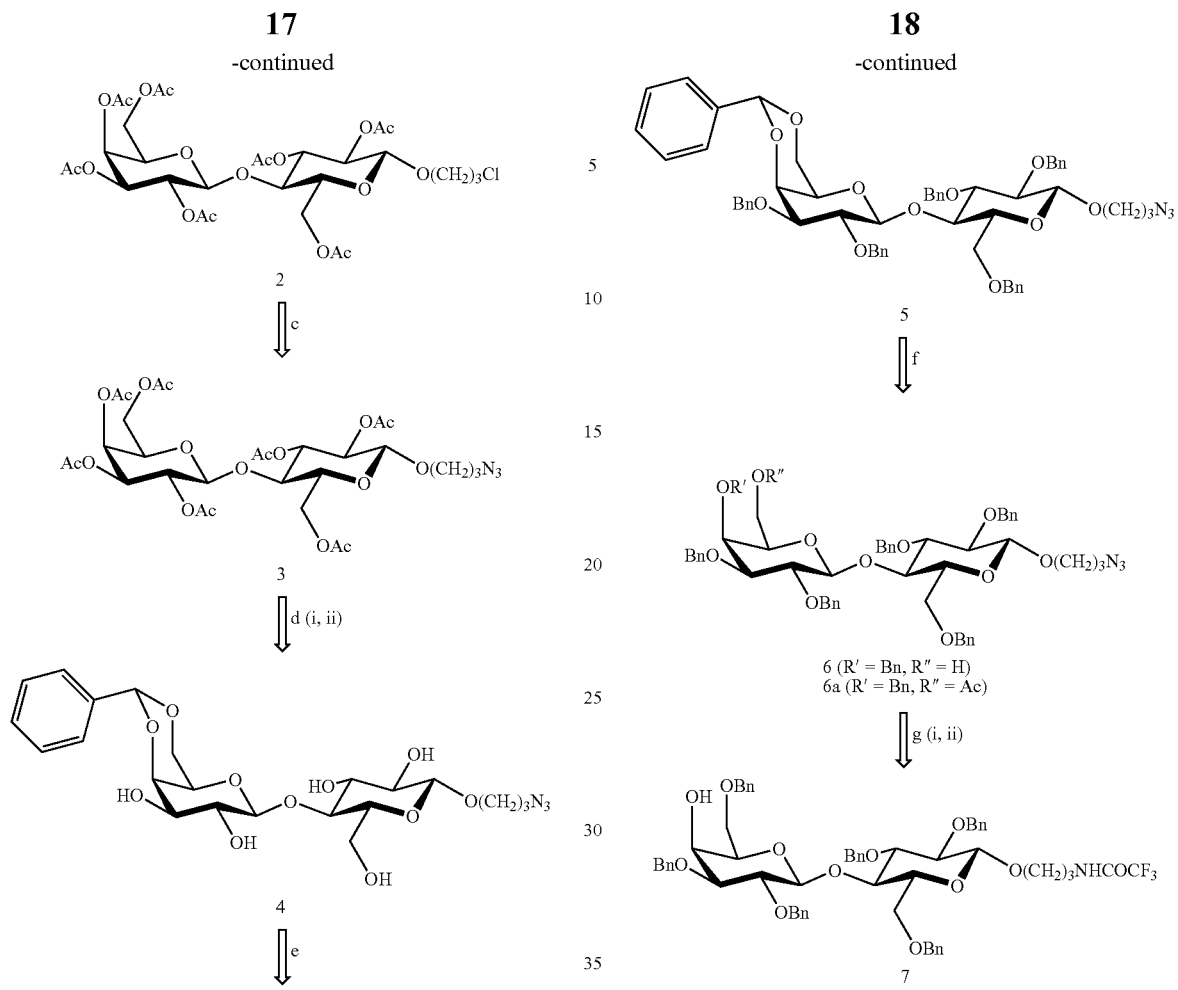
SCHEME II
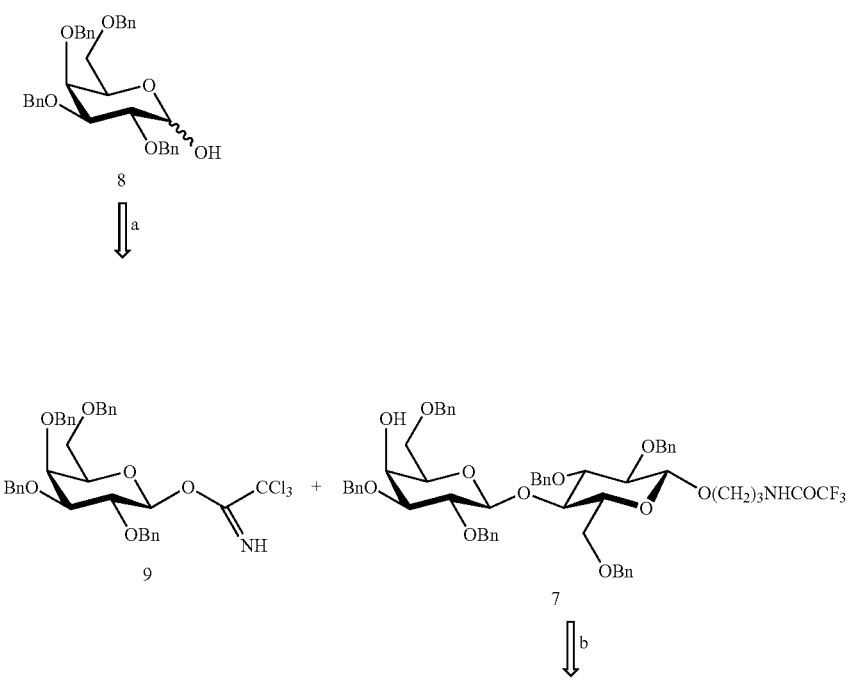

-continued
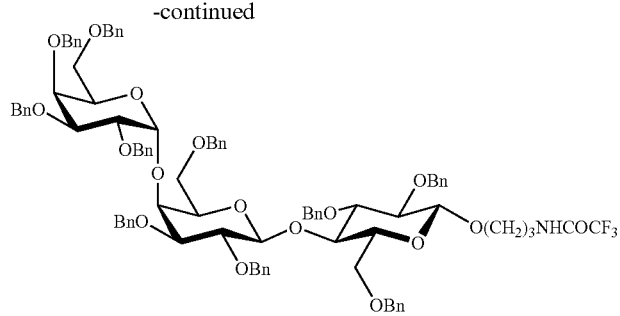
10
⇓ c, d
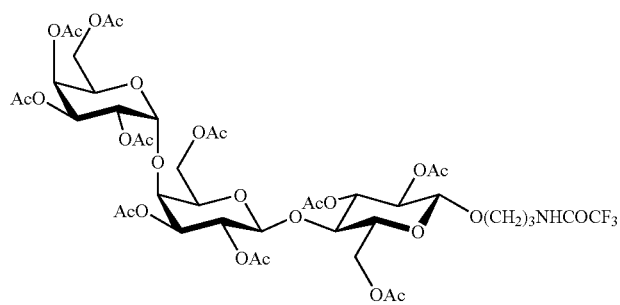
11
⇓ e, f
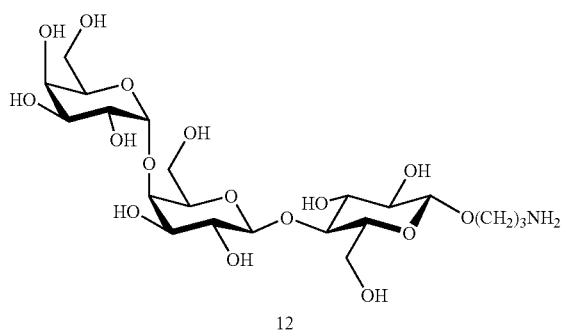
12
SCHEME III
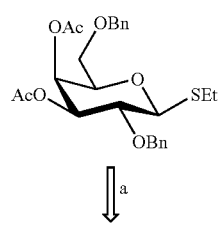
⇓ a
-continued
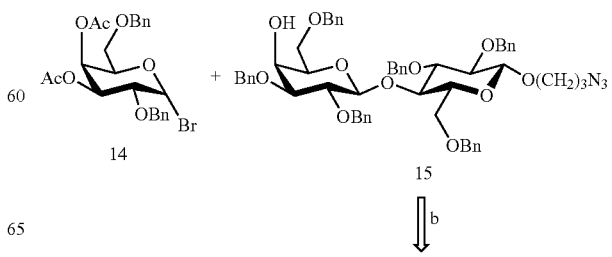
⇓ b

21
-continued
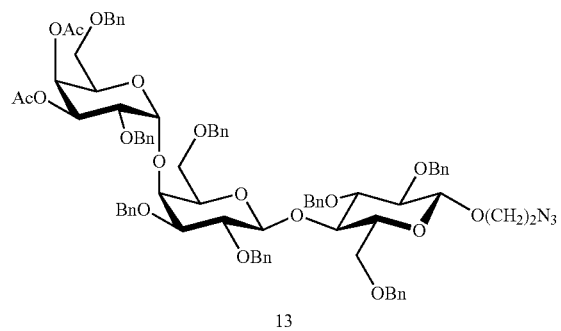
13
⇓ c
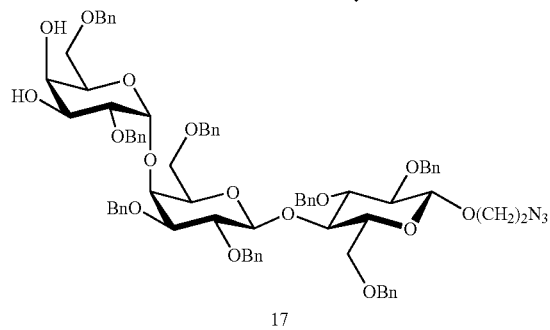
17
⇓ d
22
-continued
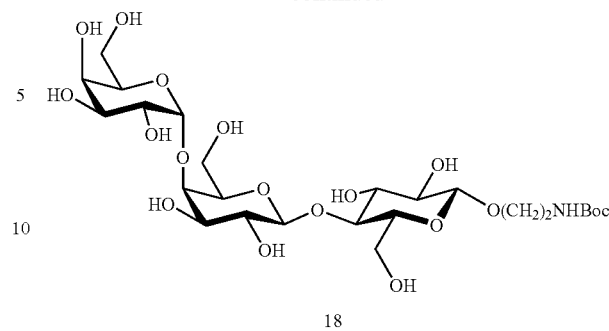
18
⇓ e
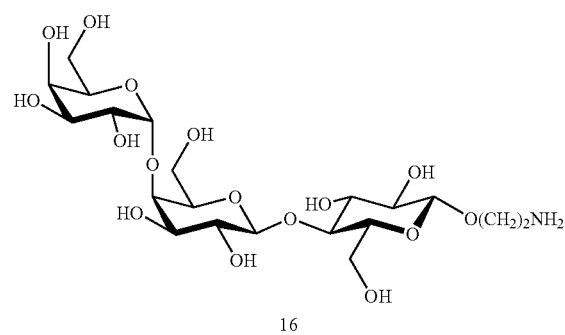
16

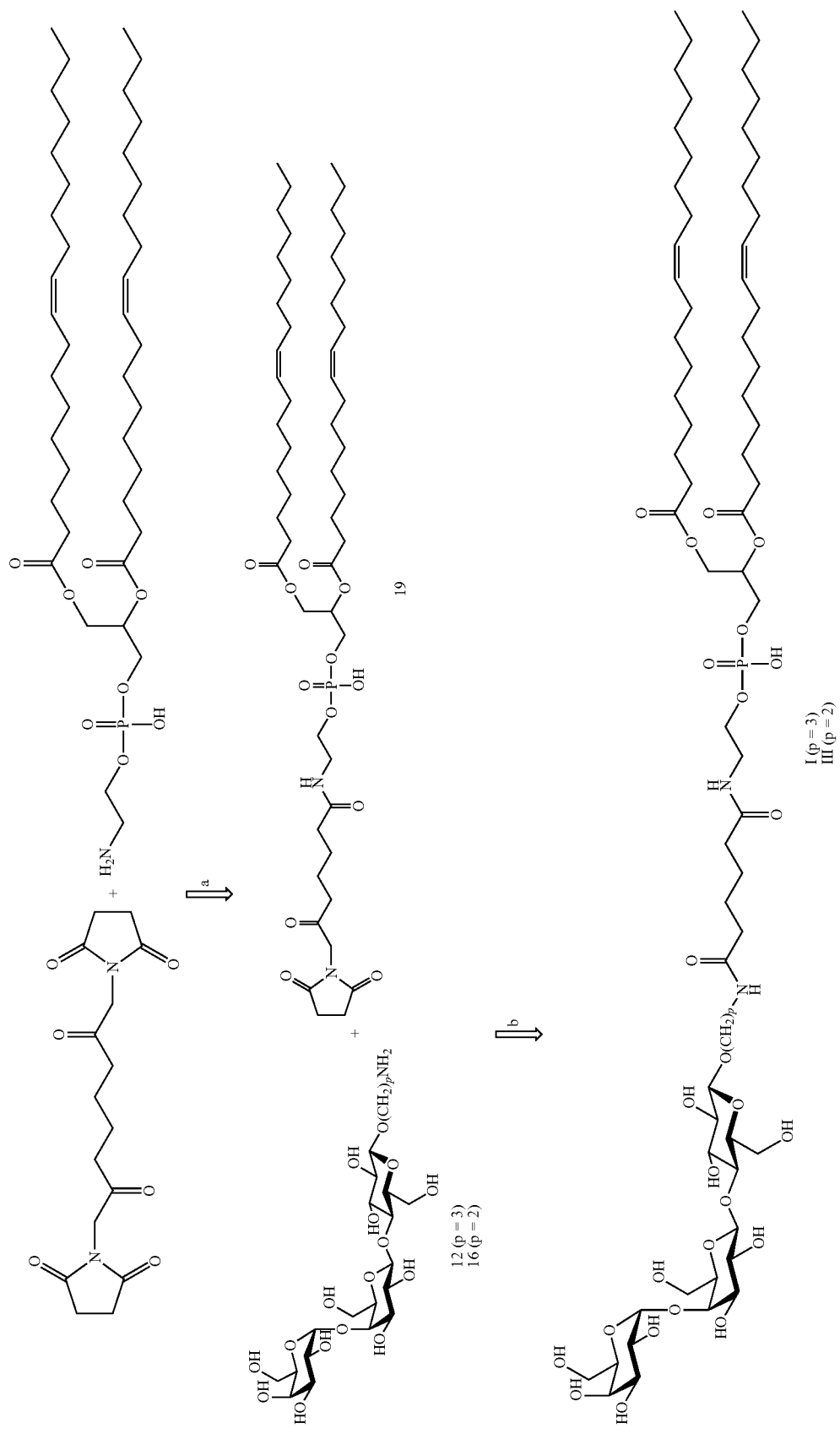

Materials and Methods

TLC was performed on Silica gel 60 (Merck, Germany) precoated plates. Spots were visualized by treating with 5% aqueous orthophosphoric acid and subsequent heating to 150° C. in the case of carbohydrates or by soaking in ninhydrin solution (3 g/l in 30:1 (v/v) butanol-acetic acid) in the case of amines.

Column chromatography was carried out on Silica gel 60 (0.040-0.063 mm, Merck, Germany). Gel chromatography was performed on Sephadex LH-20 (Pharmacia, Sweden). Solvents were removed in vacuo at 30 to 40° C.

All solvents were from KhimMed (Russia). Molecular sieves (MS 3 Å and 4 Å), trimethylsilyl trifluoromethanesulfonate, and triphenylphosphine were from Aldrich (Germany). All hydrides, 1,8-diazabicyclo[5,4,0]undec-7-ene (DBU), and trichloroacetonitrile were from Merck (Germany).

Anhydrous tetrahydrofuran (THF) and diethyl ether ($Et_2O$) were obtained by distillation from lithium aluminium hydride ($H_4AlLi$). Dichloromethane for glycoside synthesis was dried by distillation from phosphorous pentoxide and calcium hydride, and stored over molecular sieves MS 4 Å. Solid reagents were dried for 2 h in vacuo (0.1 mm Hg) at 20 to 40° C.

Deacetylation was performed according to Zemplen in anhydrous methanol. The solution of the acetylated compound was treated with 2 M sodium methylate in methanol up to pH 9. When the reaction was completed, $Na^+$ ions were removed with cation exchange resin Dowex 50X-400 ($H^+$) (Acros, Belgium). The solution was concentrated in vacuo.

Optical rotation was measured on a Jasco DIP-360 digital polarimeter at 25° C.

Mass spectra were recorded on a Vision-2000 (Thermo Bioanalysis, UK) MALDI-TOF mass spectrometer using dihydroxybenzoic acid as a matrix.

$^1H$ NMR spectra were recorded on a Bruker WM spectrometer (500 MHz) at 25° C. Chemical shifts (δ, ppm) were recorded relative to $D_2O$ (δ=4.750), $CDCl_3$ (δ=7.270), and $CD_3OD$ (δ=3.500) as internal standards. The values of coupling constants (Hz) are provided. The signals in the $^1H$ NMR spectra were assigned by suppression of spin-spin interaction (double resonance) and 2D-1H,1H-COSY experiments.

Preparation of (2,3,4,6-tetra-O-acetyl-β-D-galactopyranosyl)-(1→4)-2,3,6-tri-O-acetyl-α-D-glucopyranosyl trichloroacetimidate (1)

Trichloroacetonitrile (12.1 ml, 121 mmol) and DBU (0.45 ml, 3 mmol) were added to a solution of 1a (7.68 g, 12.1 mmol) in dry dichloromethane (150 ml) at −5° C. The reaction mixture was stirred at −5° C. for 3.5 h and concentrated in vacuo.

Flash chromatography (2:1 to 1:2 (0.1% $Et_3N$) toluene-ethyl acetate) of the residue provided 1 (6.01 g, 63.9%) as a light yellow foam, $R_f$ 0.55 (2:1 toluene-acetone).

$^1H$ NMR, $CDCl_3$: 1.95-2.2 (7s, 21H, 7Ac), 4.49 (d, 1H, $J_{1,2}$=8.07, H-1b), 4.91 (dd, 1H, $J_{3,2}$=10.3, $J_{3,4}$=2.8, H-3b), 5.05 (dd, 1H, $J_{2,1}$=3.5, $J_{2,3}$=9.3, H-2a), 5.12 (dd, 1H, $J_{2,1}$=8.07, $J_{2,3}$=10.3, H-2b), 5.32 (d, 1H, $J_{4,3}$=3, $J_{4,5}$<1, H-4b), 5.52 (t, 1H, $J_{3,2}$=$J_{3,4}$=9.29, H-3a), 6.48 (d, 1H, $J_{1,2}$=3.5, H-1a), 8.64 (s, 1H, HN=$CCCl_3$).

Preparation of 3-chloropropyl-(2,3,4,6-tetra-O-acetyl-β-D-galactopyranosyl)-(1→4)-2,3,6-tri-O-acetyl-β-D-glucopyranoside (2)

A mixture of 2.94 g (3.8 mmol) of trichloroacetimidate 1, 0.66 ml (7.5 mmol) 3-chloropropanol, 50 ml dichloromethane, and 3 g of molecular sieves MS 4 Å was cooled to −5° C. An 8% solution of $BF_3·Et_2O$ (0.4 mmol) in anhydrous dichloromethane was added drop wise with stirring.

After 30 min, the reaction mixture was filtered, diluted with chloroform (500 ml), and washed with water, saturated sodium hydrocarbonate solution, and water to pH 7. The washed reaction mixture was dried by filtration through a cotton layer and concentrated in vacuo.

Column chromatography on Silica gel (elution with 2.5:1 (v/v) toluene-ethyl acetate) resulted in 1.75 g (65%) of lactose derivative (2) as white foam. $R_f$ 0.54 (2:1 toluene-acetone), $R_f$ 0.50 (4:2:1 hexane-chloroform-isopropanol), $[α]_D$ −4° (c 1.0, $CHCl_3$), m/z 712.2 ($M^+$).

$^1H$ NMR, $CDCl_3$: 1.95 (br. s, 5H, Ac, —$CH_2$—), 2.0-2.2 (6s, 18H, 6Ac), 3.52 (m, 2H, —$CH_2Cl$), 3.63 (m, 1H, H-5a), 3.68 (m, 1H, OCHH—), 3.79 (t, 1H, J=9.3, H-4a), 3.88 (m, 1H, H-5b), 3.93-3.98 (m, 1H, OCHH—), 4.05-4.15 (m, 3H, H-6a', H-6b, H-6b'), 4.45 (d, 2H, H-1a, H-1b, $J_{2,1}$=7.83) 4.47 (m, 1H, H-6a), 4.89 (dd, 1H, $J_{2,3}$=9.3, $J_{2,1}$=7.82, H-2a), 4.96 (dd, 1H, $J_{3,2}$=10.5, $J_{3,4}$=3.42, H-3b), 5.11 (dd, 1H, $J_{2,3}$=10.5, $J_{2,1}$=7.83, H-2b), 5.21 (t, 1H, J=9.3, H-3a), 5.35 (dd, 1H, $J_{4,3}$=3.42, $J_{4,5}$<1).

Preparation of 3-azidopropyl (2,3,4,6-tetra-O-acetyl-β-D-galactopyranosyl)-(1→4)-2,3,6-tri-O-acetyl-β-D-glucopyranoside (3)

A mixture of 2.15 g (3 mmol) of trichloropropylglycoside 2, 0.59 g (9 mmol) $NaN_3$, and 30 ml DMSO was maintained at 80° C. with stirring for 20 h. The mixture was then diluted with chloroform (500 ml), washed with water (4×100 ml), dried by filtration through a cotton layer, and concentrated in vacuo.

Column chromatography on Silica gel (elution with 8:2:1 hexane-chloroform-isopropanol) resulted in 1.96 g (91%) of glycoside (3) as a white foam, $R_f$ 0.54 (2:1 (v/v) toluene-acetone), $R_f$ 0.50 (4:2:1 (v/v/v) hexane-chloroform-isopropanol), $[α]_D$ −5.4° (c 1.0, $CHCl_3$), m/z 718.8 ($M^+$).

$^1H$ NMR, $CDCl_3$: 1.85 (m, 2H, —$CH_2$—), 1.98-2.2 (7s, 21H, 7Ac), 3.36 (m, 2H, —$CH_2N_3$), 3.61 (m, 2H, H-5a, OCHH—$CH_2$—), 3.8 (t, 1H, $J_{3,4}$=$J_{4,5}$=9.29, H-4a), 3.85-3.94 (m, 2H, OCHH—$CH_2$; H-5b), 4.05-4.17 (m, 3H, H-6a, H-6a', H-6b), 4.49 (d, 1H, $J_{1,2}$=8.07, H-1a), 4.5 (m, 1H, H-6b'), 4.51 (d, 1H, $J_{1,2}$=8.07, H-1b), 4.9 (dd, 1H, $J_{2,1}$=8.07, $J_{2,3}$=9.29, H-2a), 4.97 (dd, 1H, $J_{3,2}$=10.27, $J_{3,4}$=3, H-3b), 5.12 (dd, 1H, $J_{2,1}$=8.07, $J_{2,3}$=10.27, H-2b), 5.2 (t, 1H, $J_{3,2}$=$J_{3,4}$=9.29, H-3a), 5.36 (dd, 1H, $J_{4,3}$=3, $J_{4,5}$<1).

Preparation of 3-azidopropyl (4,6-O-benzylidene-3-galactopyranosyl)-(1→4)-β-D-glucopyranoside (4)

The lactoside 3 (1.74 g, 2.4 mmol) was deacetylated according to Zemplen and co-evaporated with toluene (2×30 ml). The residue was treated with α,α-dimethoxytoluene (0.65 ml, 3.6 mmol) and p-toluenesulfonic acid (50 mg, to pH 3) in DMF (20 ml) for 3 h. The reaction mixture was then quenched with pyridine, concentrated, and co-evaporated with o-xylene.

Column chromatography on Silica gel (elution with 9:1 (v/v) chloroform-isopropanol) and recrystallization (chloroform-methanol) resulted in 0.756 mg (62%) of benzylidene derivative (4). $R_f$ 0.6 (5:1 chloroform-isopropanol), $[α]_D$ −25.7° (c 1.0, methanol), m/z 513:4 ($M^+$).

$^1H$ NMR, $CD_3OD$: 2.06 (m, 2H, —$CH_2$—), 3.45 (dd, 1H, $J_{2,1}$=$J_{2,3}$=9, H-2a), 3.61 (m, 1H, H-5a), 3.64 (m, 2H, —$CH_2N_3$), 3.74-3.9 (m, 6H, OCHH—; H-3a, H-4a; H-2b, H-3b, H-5b), 4.08-4.18 (m, 3H, H-6, H-6a', OCHH—), 4.34-4.44

(m, 3H, H-6b, H-6b', H-4b), 4.5 (d, 1H, $J_{1,2}$=7.9, H-1a), 4.68 (d, 1H, $J_{1,2}$=8, H-1b), 5.82 (s, 1H, CHPh), 7.55-7.72 (m, 5H, CHPh).

Preparation of 3-azidopropyl (4,6-O-benzylidene-3-O-benzyl-A-D-galactopyranosyl)-(1→4)-2,3,6-tri-O-benzyl-β-D-glucopyranoside (5)

Sodium hydride in mineral oil (290 mg, 12 mmol) was slowly added in 4 to 5 portions to a solution of 4 (726 mg, 1.5 mmol) in DMF (15 ml) at 0° C. with stirring. After 1 h, the ice bath was removed and benzyl bromide was added drop wise. The mixture was stirred overnight. 10 ml of methanol was then added. After 1 h, the mixture was diluted with chloroform (500 ml), and washed with water (3×200 ml), dried by filtration through a cotton layer, concentrated, and co-evaporated in vacuo with o-xylene.

Column chromatography on Silica gel (elution with 10:1 toluene-ethyl acetate) resulted in 1.24 g (87%) of lactose derivative 5 as white foam, $R_f$ 0.56 (5:3 (v/v) hexane-ethyl acetate), $[\alpha]_D$ +10.8° (c 1.0, CHCl$_3$), m/z 963.8 (M$^+$).

$^1$H NMR, CDCl$_3$: 1.85 (m, 2H, —CH$_2$—), 2.91 (m, 1H, H-5b), 3.33 (m, 1H, H-5a), 3.34-3.42 (m, 4H, H-2a, H-3b, —CH$_2$N$_3$), 3.55-3.62 (m, 2H, OCHH—; H-3a), 3.73 (dd, 1H, $J_{2,1}$=8, $J_{2,3}$=10, H-2b), 3.92-3.97 (m, 2H, H-4a, OCHH—), 4.0 (br. d, 1H, $J_{4,3}$=3.6, H-4b), 4.34 (d, 1H, $J_{1,2}$=7.9, H-1a), 4.42 (d, 1H, $J_{1,2}$=8, H-1b), 5.43 (s, 1H, CH(Bd), 7.14-7.50 (m, 30H, Ph).

Preparation of 3-azidopropyl (2,3,6-O-tri-O-benzyl-β-D-galactopyranosyl)-(1→4)-2,3,6-tri-O-benzyl-β-D-glucopyranoside (6)

Hydrogen chloride in diethyl ether was added to a mixture of 5 (1.24 g, 1.3 mmol), sodium cyanoborohydride (0.57 g, 9.1 mmol), and freshly activated molecular sieves MS 3 Å (33 g) in anhydrous THF (20 ml) until the evolution of gas ceased.

The mixture was stirred for 2 h, diluted with chloroform (300 ml), washed with water, saturated sodium hydrocarbonate solution, and water to pH 7. The washed mixture was dried by filtration through a cotton layer and concentrated in vacuo.

Column chromatography on Silica gel (elution with 20:1 to 7:3 (v/v) toluene-ethyl acetate) resulted in 0.91 g (65%) of lactose derivative 6 as a white foam, $R_f$ 0.42 (9:1 (v/v) toluene-acetone), $[\alpha]_D$ +17.8° (c 1.0, CHCl$_3$), m/z 965.8 (M$^+$).

$^1$H NMR, CDCl$_3$: 1.85 (m, 2H, —CH$_2$—), 2.39 (d, 1H, J=2.2, OH), 4.04 (br. s, 1H, H-4b), 4.34 (d, 1H, $J_{1,2}$=7.9, H-1a), 4.42 (d, 1H, $J_{1,2}$=8, H-1b), 7.14-7.50 (m, 30H, Ph).

$^1$H NMR of acetylated analytical probe 6a, CDCl$_3$: 1.85 (m, 2H, —CH$_2$—), 4.34 (d, 1H, $J_{1,2}$=7.9, H-1a), 4.42 (d, 1H, $J_{1,2}$=8, H-1b), 5.5 (br. d, 1H, $J_{4,3}$=3.43, H-4b), 7.14-7.50 (m, 30H, Ph).

Preparation of 3-trifluoroacetamidopropyl (2,3,6-O-tri-O-benzyl-β-D-galactopyranosyl)-(1→4)-2,3,6-tri-O-benzyl-β-D-glucopyranoside (7)

A mixture of derivative 6 (0.914 g, 0.94 mmol), triphenylphosphine (0.5 g, 1.9 mmol) and THF (10 ml) was stirred for 0.5 h, 100 µl of water added, and the mixture stirred overnight. The reaction mixture was then concentrated and co-evaporated with methanol. The residue was dissolved in methanol (15 ml) and triethylamine (30 µl) and methyl trifluoroacetate (0.48 ml, 4.7 mmol) added. The solution was held for 30 min and then concentrated.

Column chromatography on Silica gel (elution with 5:1 to 1:1 (v/v) hexane-acetone) resulted in 0.87 g (84%) of lactose derivative 7 as white foam, $R_f$ 0.49 (9:1 (v/v) hexane-acetone), $[\alpha]_D$ +17° (c 1.0, CHCl$_3$), m/z 1060.1 (M$^+$+Na).

$^1$H NMR, CDCl$_3$: 1.88 (m, 2H, —CH$_2$—), 2.40 (br. s, 1H, OH), 4.05 (br. s, 1H, H-4b), 4.36 (d, 1H, $J_{1,2}$=7.8, H-1a), 4.40 (d, 1H, $J_{1,2}$=7.6, H-1b), 7.10-7.35 (m, 30H, Ph).

Preparation of 2,3,4,6-tetra-O-benzyl-β-D-galactopyranosyl trichloroacetimidate (9)

A mixture of galactose derivative 8 (2 g, 3.65 mmol), trichloroacetonitrile (1.75 ml, 17.55 mmol), anhydrous potassium carbonate (2 g, 14.6 mmol), and dichloromethane (4 ml) was stirred for 22 h at room temperature under argon. The mixture was then filtered through a Celite layer and concentrated in vacuo. Column chromatography on Silica gel (elution with 4:1 (v/v) hexane-ethyl acetate (1% Et$_3$N) resulted in 1.5 g (60%) of 9 as white foam, $R_f$ 0.47 (7:3 (v/v) hexane-ethyl acetate containing 1% Et$_3$N) and 0.46 g (0.8 mmol, 23%) of the starting derivative 8, $R_f$ 0.27 (7:3 (v/v) hexane-ethyl acetate containing 1% Et$_3$N).

$^1$H NMR (CDCl$_3$): 3.60-3.70 (m, 3H, H-3, H-6, R-6'), 3.75 (t, 1H, $J_{5,6}$=6.30, H-5), 3.98 (d, 1H, $J_{4,3}$=2.19, H-4), 4.08 (dd, 1H, $J_{2,3}$=9.73, $J_{2,1}$=7.95, H-2), 4.42 and 4.47 (ABq, 2H, J=12.00, PhCH$_2$), 4.63 and 4.95 (ABq, 2H, J=11.51, PhCH$_2$), 4.72 (s, 2H, PhCH$_2$), 4.80 and 4.90 (ABq, 2H, J=10.95, PhCH$_2$), 5.74 (d, 1H, $J_{1,2}$=7.95, H-1), 7.22-7.35 (m, 20H, ArH), 8.62 (s, 1H, NH).

Preparation of 3-trifluoroacetamidopropyl (2,3,4,6-tetra-O-benzyl-α-D-galactopyranosyl)-(1→4)-(2,3,6-tri-O-benzyl-β-D-galactopyranosyl)-(1→4)-2,3,6-tri-O-benzyl-β-D-glucopyranoside (10)

A mixture of lactose derivative 7 (158 mg, 0.153 mmol), trichloroacetimidate 9 (120 mg, 0.175 mmol), molecular sieves MS 4 Å (0.5 g), and dichloromethane (5 ml) was stirred for 30 min at room temperature under argon. 0.1 ml of a 1% (v/v) solution of trimethylsilyl trifluoromethanesulfonate in dichloromethane was then added. After 2 h, another 50 mg (0.073 mmol) trichloroacetimidate 9 and 30 µl of a 1% (v/v) solution of trimethylsilyl trifluoromethanesulfonate in dichloromethane were added. The reaction mixture was stirred overnight at +4° C., quenched with triethylamine (5 µl), filtered, and concentrated in vacuo.

Column chromatography on Silica gel (elution with 12:1 to 1:1 (v/v) toluene-ethyl acetate) resulted in 170 mg (72%) of trisaccharide 10; $R_f$ 0.56 (4:1 (v/v) toluene-ethyl acetate); $[\alpha]_D$ +30.8° (c 1.0, CHCl$_3$).

$^1$H NMR, CDCl$_3$: 1.78-1.89 (m, 2H, —CH$_2$—), 4.34 (d, 1H, $J_{1,2}$=7.8, H-1a), 4.43 (d, 1H, $J_{1,2}$=7.4, H-1b), 5.06 (d, 1H, $J_{1,2}$=3.0, H-1c), 7.14-7.48 (m, 50H, Ph).

Preparation of 3-trifluoroacetamidopropyl (2,3,4,6-tetra-O-acetyl-α-D-galactopyranosyl)-(1→4)-(2,3,6-tri-O-acetyl-β-D-galactopyranosyl)-(1→4)-2,3,6-tri-O-acetyl-β-D-glucopyranoside (11)

The catalyst 10% Pd/C (10 mg) was added to a solution of the protected oligosaccharide 10 (73 mg, 0.047 mmol) in methanol (7 ml), the mixture degassed, and the flask filled with hydrogen. The reaction mixture was stirred for 1 h, filtered off from the catalyst through a Celite layer, and concentrated in vacuo. The dry residue was dissolved in pyridine (2 ml), acetic anhydride (1 ml) added, and the mixture held for 3 h. The solvents were then evaporated and residue co-evaporated with toluene (4×2 ml).

Column chromatography on Silica gel (elution with 2:1 hexane-acetone) resulted in 43.5 mg (90%) of trisaccharide 11 as a white foam, $R_f$ 0.52 (2:1 hexane-acetone), $[\alpha]_D$ +30.4° (c 1.0, CHCl$_3$).

$^1$H NMR, CDCl$_3$: 1.87 (2H, m, CH$_2$); 1.99, 2.05, 2.05, 2.06, 2.07, 2.07, 2.09, 2.09, 2.12, and 2.14 (10×3H, 10 s, 10 Ac); 3.37 and 3.52 (2×1H, 2 m, 2 CHN); 3.63 (1H, ddd, $J_{4,5}$=9.8, $J_{5,6}$=4.9, $J_{5,6'}$=2.0, H-5a); 3.72 (1H, m, OCH); 3.77 (1H, ddd≈br. т, $J_{4,5}$<1, $J_{5,6}$=6.8, $J_{5,6}$=6.1, H-5b); 3.79 (1H, dd, $J_{3,4}$=9.3, $J_{4,5}$=9.8, H-4a); 3.87 (1H, m, OCH); 4.02 (1H, dd≈br. d, $J_{3,4}$=2.5, $J_{4,5}$<1, H-4b); 4.09 (1H, dd, $J_{5,6}$=4.9, $J_{6,6'}$=12.0, H-6a); 4.12 (1H, dd, $J_{5,6}$=5.6, $J_{6,6'}$=10.8, H-6c); 4.14 (1H, dd, $J_{5,6}$=6.8, $J_{6,6'}$=11.0, H-6b); 4.17 (1H, dd, $J_{5,6}$=8.6, $J_{6,6'}$=10.8, H-6'c); 4.45 (1H, dd, $J_{5,6}$=6.1, $J_{6,6'}$=11.0, H-6'b); 4.49 (1H, ddd □ br. т, $J_{4,5}$<1, $J_{5,6}$=5.6, $J_{5,6}$=8.6, H-5c); 4.50 (1H, d, $J_{1,2}$=7.8, H-1a); 4.55 (1H, d, $J_{1,2}$=7.8, H-1b); 4.59 (1H, dd, $J_{5,6}$=2.0, $J_{6,6'}$=12.0, H-6'a); 4.76 (1H, dd, $J_{2,3}$=10.8, $J_{3,4}$=2.5, H-3b); 4.86 (1H, dd, $J_{1,2}$=8.1, $J_{2,3}$=9.5, H-2a); 4.10 (1H, d, $J_{1,2}$=3.4, H-1c); 5.12 (1H, dd, $J_{1,2}$=7.8, $J_{2,3}$=10.8, H-2b); 5.19 (1H, dd, $J_{1,2}$=3.4, $J_{2,3}$=11.0, H-2c); 5.22 (1H, dd≈т, $J_{2,3}$=9.5, $J_{3,4}$=9.3, H-3a); 5.40 (1H, dd, $J_{2,3}$=11.0, $J_{3,4}$=3.4, H-3c); 5.59 (1H, dd≈br. d, $J_{3,4}$=3.4, $J_{4,5}$<1, H-4c); 7.09 (1H, m, NHCOCF$_3$).

Preparation of 3-aminopropyl α-D-galactopyranosyl-(1→4)-β-D-galactopyranosyl-(1→4)-β-D-glucopyranoside (Gb$_3$-sp3) (12)

Sodium methylate (30 μl of 2 M solution in methanol) was added to a solution of trisaccharide (11) (43 mg, 0.042 mmol) in anhydrous methanol (3 ml) and held for 2 h. The solution was then concentrated in vacuo, water (3 ml) added, and the mixture held for 3 h. The mixture was then applied to a column (10×50 mm) with Dowex 50X4-400 (H$^+$) cation exchange resin.

The target compound was eluted with 1 M aqueous ammonia and the eluant concentrated in vacuo. Lyophilization from water provided trisaccharide 12 (23 mg, quant.) as a colorless powder. $R_f$ 0.3 (100:10:10:10:2 (v/v/v/v/v) ethanol-n-butanol-pyridine-water-acetic acid), $[\alpha]_D$ +42° (c 1; water), m/z 584.9 (M$^+$+Na).

$^1$H NMR, D$_2$O: 1.98-2.05 (m, 2H, —CH$_2$—), 3.17 (m, 2H, —CH$_2$NH$_2$), 3.33-3.35 (m, 1H, H-2a), 4.36 (m, 1H, H-5c), 4.53 (d, 2H, J=7.8, H-1a, H-1b), 4.97 (d, 1H, $J_{1,2}$=3.67, H-1c).

Preparation of 2-azidoethyl (3,4-di-O-acetyl-2,6-di-O-benzyl-α-D-galactopyranosyl)-(1→4)-(2,3,6-tri-O-benzyl-β-D-galactopyranosyl)-(1→4)-2,3,6-tri-O-benzyl-β-D-glucopyranoside (13)

To the solution of ethyl 3,4-di-O-acetyl-2,6-di-O-benzyl-1-thio-β-D-galactopyranoside (550 mg, 1.11 mmol) in dichloromethane (10 ml) was added Br$_2$ (57 μl, 1.11 mmol). The mixture was held for 20 min at room temperature, then concentrated in vacuo at room temperature and co-evaporated with anhydrous benzene (3×30 ml). The crude 3,4-di-O-acetyl-2,6-di-O-benzyl-α-D-galactopyranosylbromide (14) was used for glycosylation without purification.

The mixture of lactose derivative 15 (Sun et al (2006)) (500 mg, 0.525 mmol), 1,1,3,3-tetramethylurea (300 μl), molecular sieves MS 4 Å (1 g), and dichloromethane (25 ml) was stirred for 30 min at room temperature. Silver trifluoromethanesulfonate (285 mg, 1.11 mmol), molecular sieves MS 4 Å (0.5 g), and the freshly prepared galactopyranosyl-bromide (14) in dichloromethane (15 ml) were then added. The reaction mixture was stirred overnight, filtered, and concentrated in vacuo.

Column chromatography on Silica gel (elution with 3:1 to 1:1 (v/v) hexane-ethyl acetate) resulted in 570 mg (79%) of trisaccharide 13, $R_f$ 0.25 (2:1 (v/v) hexane-ethyl acetate); $[\alpha]_D$ +32° (c 0.8, CHCl$_3$)

$^1$H NMR, CDCl$_3$: 1.88, 1.94 (2s, 2Ac), 3.00 (dd, 1H, $J_{5,6}$=4.9, $J_{6',6}$=8.4, H-6a), 3.19 (dd, $J_{1,2}$=8.5, $J_{2,3}$=8.9, H-2a), 3.30-3.36 (m, 2H, —CHHN$_3$, H-6'a), 3.38-3.47 (m, 4H, H-5a, H-5b, H-2b, H-6b), 3.48-3.54 (m, 1H, —CHHN$_3$), 3.61 (dd, 1H, $J_{2,3}$=8.9, $J_{3,4}$=9.2, H-3a), 3.69-3.75 (m, 3H, H-6'b, H-6c, —OCHH—), 3.85 (dd, 1H, $J_{5,6}$=4.6, $J_{6,6}$=11.0, H-6c), 3.89 (dd, 1H, $J_{1,2}$=3.4, $J_{2,3}$=10.8, H-2c), 3.95 (dd, 1H, $J_{3,4}$=9.2, $J_{4,5}$=9.5, H-4a), 4.0-4.1 (m, 4H, —OCHH—, H-4b, CH$_2$Ph), 4.25, 4.29, 4.32, 4.39 (4 d, 4×1H, $J_{AB}$=12, 4-CHPh), 4.43 (d, 1H, $J_{1,2}$=7.6, H-1), 4.48 (d, 1H, $J_{1,2}$=7.6, H-1), 4.54-4.62 (m, 5H, 4-CHPh, H-5c), 4.71-4.84 (m, 4H, 4-CHPh), 4.89, 4.91, and 5.09 (3 d, 3×1H, 3 4-CHPh), 5.15 (d, 1H, $J_{1,2}$=3.0, H-1c), 5.39 (dd, 1H, $J_{2,3}$=10.8, $J_{3,4}$=3.4, H-3c), 5.56 (dd, 1H, $J_{3,4}$=3.4, $J_{4,5}$=0.9, H-4c), 7.14-7.48 (m, 40H, Ph).

Preparation of 2-aminoethyl α-D-galactopyranosyl-(1→4)-β-D-galactopyranosyl-(1→4)-β-D-glucopyranoside (Gb$_3$-sp2) (16)

Sodium methylate (100 μl of 2 M solution in methanol) was added to a suspension of trisaccharide (13) (500 mg, 0.363 mmol) in anhydrous methanol (50 ml). The mixture was stirred overnight at room temperature, quenched with acetic acid, and concentrated in vacuo.

Column chromatography on Silica gel (elution with 2:1 to 1:1 (v/v) hexane-ethyl acetate) resulted in 470 mg of trisaccharide (17), $R_f$ 0.5 (1:1 (v/v) hexane-ethyl acetate), $[\alpha]_D$ +36° (c 0.5, CHCl$_3$).

To a solution of trisaccharide (17) and Boc$_2$O ((150 mg, 0.91 mmol) in anhydrous methanol (50 ml) was added the catalyst 10% Pd/C (500 mg). The mixture was degassed and the flask filled with hydrogen. The reaction mixture was stirred for 3 h, filtered off from the Pd/C, and concentrated in vacuo.

Column chromatography on Silica gel (elution with 6:5:1 (v/v/v) chloroform-ethanol-water) resulted in 160 mg (68%) of trisaccharide 18 $R_f$ 0.3 (6:5:1 (v/v/v) dichloromethane-ethanol-water). $^1$H NMR, D$_2$O: 1.45 (s, 9H, (CH$_3$)$_3$COCO—), 4.53 (d, 1H, $J_{1,2}$=7.8, H-1b), 4.58 (d, 1H, $J_{1,2}$=7.4, H-1b), 4.98 (d, 1H, $J_{1,2}$=3.0, H-1c).

The trisaccharide 18 was then treated with 95% CF$_3$COOH (5 ml, 10 min). Upon completion, the mixture was concentrated in vacuo, co-evaporated with toluene, and applied to a column (10×100 mm) of Dowex 50X4-400 (H$^+$) cation exchange resin. The target compound was eluted with 1 M aqueous ammonia and the eluant was concentrated in vacuo. Lyophilization from water provided trisaccharide 16 (135, quant.) as a colorless powder. $R_f$ 0.35 (100:10:10:10:2 (v/v/v/v/v) ethanol-n-butanol-pyridine-water-acetic acid), $[\alpha]_D$ +25° (c 0.2; water).

$^1$H NMR, D$_2$O: 3.32 (m, 2H, —CH$_2$NH$_2$), 3.40-3.45 (m, 1H, H-2a), 3.63 (dd, 1H, $J_{1,2}$=7.9, $J_{2,3}$=10.3, H-2b), 3.66-3.78 (m, 5H, 5a, H-3a, H-4a, H-6c, H-6'c), 3.8 (dd, 1H, $J_{3,4}$=3.1, $J_{3,2}$=10.3, H-3b), 3.84 (m, 2H, $J_{5,6}$=4.4, $J_{5,6'}$=7.9, H-5b), 3.88-3.92 (m, 3H, H-2c, H-6b, —OCHH—), 3.96 (dd, 1H, $J_{3,4}$=3.3, $J_{3,2}$=10.3, H-3c), 3.98-4.03 (m, 2H, H-6a, H-6'b), 4.06 (dd, 1H, $J_{5,6}$=2.2, $J_{6,6}$=12.3, H-6'a), 4.08 (dd, 1H, $J_{3,4}$=3.3, $J_{4,5}$=0.9, H-4c), 4.09 (d, 1H, $J_{3,4}$=3.1, H-4b), 4.17-4.21 (m, 1H, —OCHH—), 4.41 (m, 1H, H-5c), 4.56 (d, 1H, J=7.9, H-1b), 4.60 (d, 1H, J=8.1, H-1a), 5.00 (d, 1H, $J_{1,2}$=3.9, H-1c).

Preparation of activated 1,2-O-dioleoyl-sn-glycero-3-phosphatidylethanolamine (Ad-DOPE) (19)

A solution of DOPE (40 μmol) in chloroform (1.5 ml) and triethylamine (7 μl) were added to a solution of bis(N-hydroxysuccinimidyl) adipate (200 μmol) in dry N,N-dimethylformamide (1.5 ml). The mixture was kept for 2 h at room temperature, quenched with acetic acid, and partially concentrated in vacuo.

Gel filtration on Sephadex LH-20 (1:1 (v/v) chloroform-methanol containing 0.2% acetic acid) of the residue yielded the activated lipid (37 mg, 95%) as a colorless syrup; $R_f$ 0.5 (6:3:0.5 (v/v/v) chloroform-methanol-water).

$^1$H NMR (2:1 CDCl$_3$-CD$_3$OD): 5.5 [m, 4H, 2×(—CH═CH—)], 5.39 (m, 1H, —OCH$_2$—CHO—CH$_2$O—), 4.58 (dd, 1H, J=3.67, J=11.98, —CCOOHCH—CHO—CH$_2$O—), 4.34 (dd, 1H, J=6.61, J=11.98, —CCOOHCH—CHO—CH$_2$O—), 4.26 (m, 2H, PO—CH$_2$—CH$_2$—NH$_2$), 4.18 (m, 2H, —CH$_2$—OP), 3.62 (m, 2H, PO—CH$_2$—CH$_2$—NH$_2$), 3.00 (s, 4H, ONSuc), 2.8 (m, 2H, —CH$_2$—CO (Ad)), 2.50 [m, 4H, 2×(—CH$_2$—CO)], 2.42 [m, 2H, —CH$_2$—CO (Ad)], 2.17 [m, 8H, 2×(—CH$_2$—CH═CH—CH$_2$—)], 1.93 (m, 4H, COCH$_2$CH$_2$CH$_2$CH$_2$CO), 1.78 [m, 4H, 2×(COCH$_2$CH$_2$—)], 1.43, 1.47 (2 br. s, 40H, 20 CH$_2$), 1.04 (m, 6H, 2CH$_3$).

Preparation of Gb$_3$-sp3-Ad-DOPE (I) and Gb$_3$-sp2-Ad-DOPE (III)

To a solution of activated DOPE (19) (10.5 μmol) in dichloromethane (300 μl) was added (12) or (16) (10 μmol) in DMF (0.5 ml) and then triethylamine (3 μl). The mixture was kept for 2 h at room temperature. Gel filtration on Sephadex LH-20 (1:1 (v/v) chloroform-methanol) of the mixture yielded (I) or (III) (90-95%).

Gb$_3$-sp3-Ad-DOPE (I) was determined to have a molecular weight (MW) of 1415.7 and $^1$H NMR (CDCl$_3$/CD$_3$OD, 2:1), δ: 5.5 (m, 4H, 2×(—CH═CH—), 5.43-5.39 (m, 1H, —OCH—CHO—CH$_2$O—), 5.13 (d, 1H, J=3.6, H-1 Gal), 4.61-4.58 (m, 2H; J=7.1, H-1 (Gal); J=3.7, J=12.1, —CCOOHCH—CHO—CH$_2$O—), 4.46 (d, J=7.9, H-1 Gal), 2.53-2.48 (m, 4H, 2×(—CH$_2$—CO), 2.42-2.7 (m, 4H, COCH$_2$CH$_2$CH$_2$CO), 2.21-2.16 (m, 8H, 2×(—CH$_2$—CH═CH—CH$_2$—), 2.00-1.95 (m, 2H, O—CH$_2$CH$_2$—NH), 1.78 (m, 8H, COCH$_2$CH$_2$CH$_2$CH$_2$CO and 2×(COCH$_2$CH$_2$—), 1.50, 1.47 (2 bs, 40H, 20 CH$_2$), 1.05 (m, 6H, 2CH$_3$) (FIG. 1).

Gb$_3$-sp2-Ad-DOPE (III) was determined to have a molecular weight (MW) of 1415.7 and $^1$H NMR (CDCl$_3$/CD$_3$OD, 2:1), δ: 5.5 (m, 4H, 2×(—CH═CH—), 5.43-5.39 (m, 1H, —OCH$_2$—CHO—CH$_2$O—), 5.13 (d, 1H, J=3.6, H-1 Gal), 4.61-4.58 (m, 2H; J=7.1, H-1 (Gal); J=3.7, J=12.1, —CCOOHCH—CHO—CH$_2$O—), 4.46 (d, J=7.9, H-1 Gal), 2.53-2.48 (m, 4H, 2×(—CH$_2$—CO), 2.42-2.37 (m, 4H, COCH$_2$CH$_2$CH$_2$CO), 2.21-2.16 (m, 8H, 2×(—CH$_2$—CH═CH—CH$_2$—), 1.78 (m, 8H, COCH$_2$CH$_2$CH$_2$CH$_2$CO and 2×(COCH$_2$CH$_2$—), 1.50, 1.47 (2 bs, 40H, 20CH$_2$), 1.05 (m, 6H, 2CH$_3$).

In Vitro Studies
Inhibition of Infection of Jurkat Cells with a Pseudoenvelope-Typed HIV The ability of Gb$_3$-sp3-Ad-DOPE (I) to inhibit infection by a pseudoenvelope-typed HIV having an outer envelope derived from the mouse vesticular stomatitis virus (VSV) and having an ENV-minus modified HIV genome derived from the X4 HIV-1 NL4-3 virus was evaluated.

Figure 2:
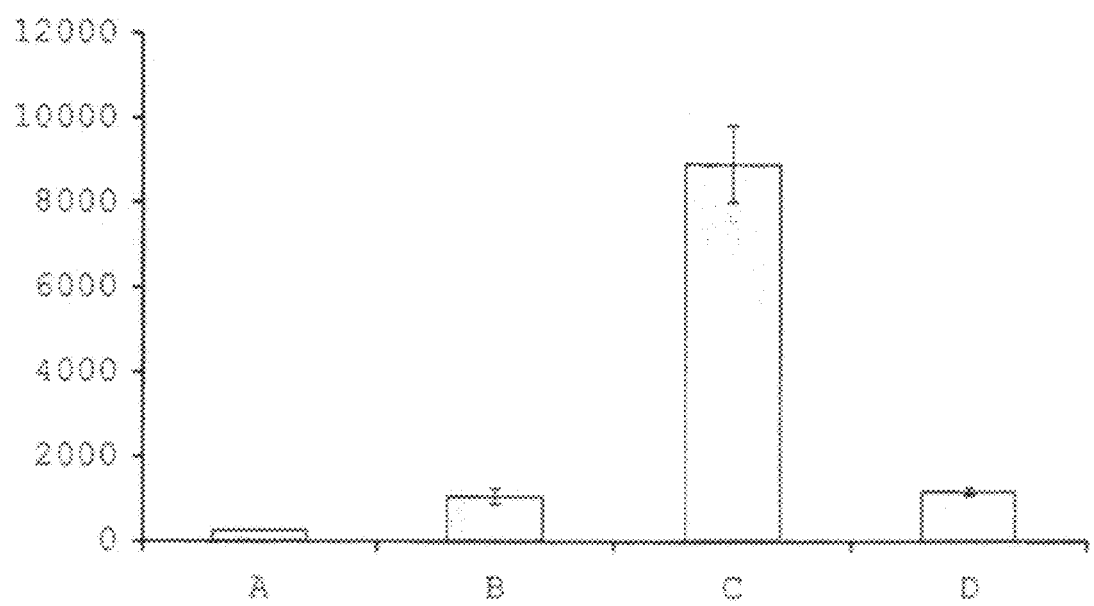
FIG. 2. Effect of 250 μM Gb$_3$-sp3-Ad-DOPE (I) on VSV/HIV infection in Jurkat Cells (RLU): A—Control; B—AZT; C—VSV/HIV; and D—250 μM Gb$_3$-sp3-Ad-DOPE (I).

The methods described mutatis mutandis in the publication of Lund et al. (2006) were used to evaluate the ability of 250 μM Gb$_3$-sp3-Ad-DOPE (I) to inhibit infection of Jurkat cells by the pseudoenvelope-typed HIV. The carbohydrate-lipid construct was demonstrated to inhibit infection by the VSV pseudoenvelope-typed virus (FIG. 2).

The ability of AZT to inhibit infection was used as a positive control.

Dose Response for Inhibition of Infection with a Pseudoenvelope-Typed HIV

HIV-1$_{IIIB}$, an X4 type, T-cell-tropic HIV virus, was sourced from the National Institutes of Health AIDS Research and Reference Reagent Program. The virus was handled in a Level III biocontainment facility. A multiplicity of infection (m.o.i) of 0.7 was used.

Gb$_3$-sp3-Ad-DOPE (I) in powdered form was dissolved in phosphate buffered saline to provide a stock solution of 6 mM. The stock solution was diluted to 2 mM to provide a working concentration.

HIV-1$_{IIIB}$ was incubated with Gb$_3$-sp3-Ad-DOPE (I) at concentrations of 50 at 1000 μM for 1 hour at 37° C. prior to incubation with Jurkat cells. Incubations were in a total volume of 100 μL.

A suspension of Jurkat cells at a density of 5×10$^5$ per mL in 100 μL complete RPMI1640 medium was incubated with a solution of untreated or treated (pre-incubated with Gb$_3$-sp3-Ad-DOPE (I) virus for 1 hour at 37° C.

Incubated cells were washed four times with phosphate buffered saline without MgCl$_2$/CaCl$_2$ and then cultured in 2 mL of complete RPMI1640 medium for a total of 5 days. On days 0, 3, 4 and 5 500 μL aliquots of culture supernatant were taken.

Aliquots of culture supernatant were stored at −80° C. A determination of the level of HIV p24 core protein was conducted by ELISA (Coulter) for the supernatant of the Day 4 supernatant.

Figure 3:
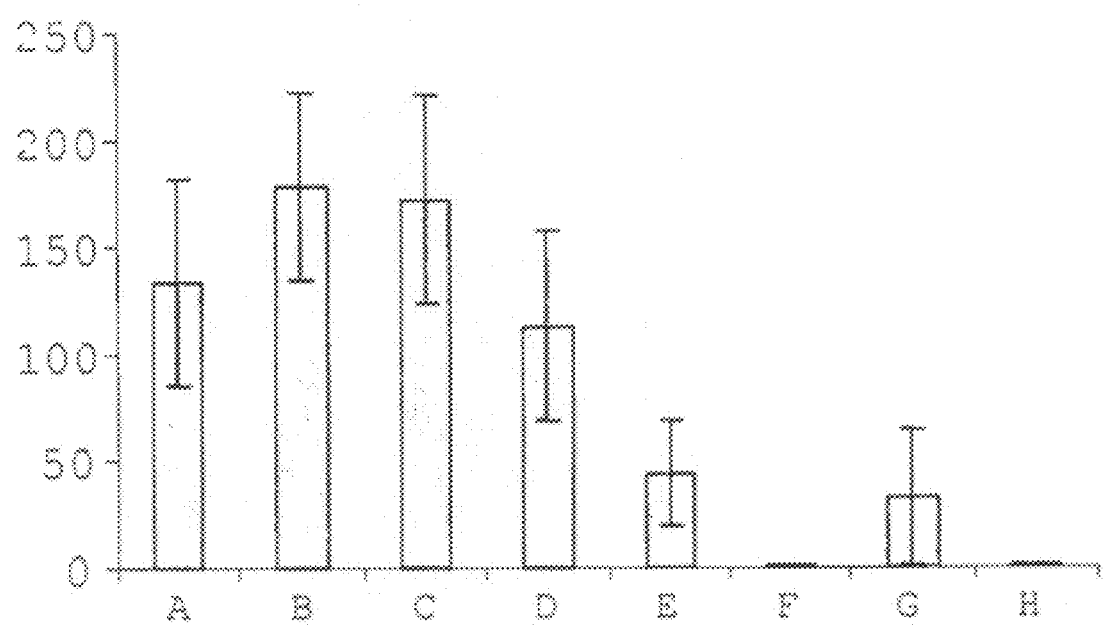
FIG. 3. Inhibition of infection of Jurkat cells by pre-incubation of X4 HIV-1$_{IIIB}$ with the carbohydrate-lipid construct designated Gb$_3$-sp3-Ad-DOPE (I) (p24 pg/mL)(r=4): A—Control; B—50 μM; C—100 μM; D—200 μM; E—400 μM; F—600 μM; G—800 μM; and H—1000 μM.

Results for quadruplicate experiments (r=4) are presented in Table 1 and FIG. 3.

Figure 4:
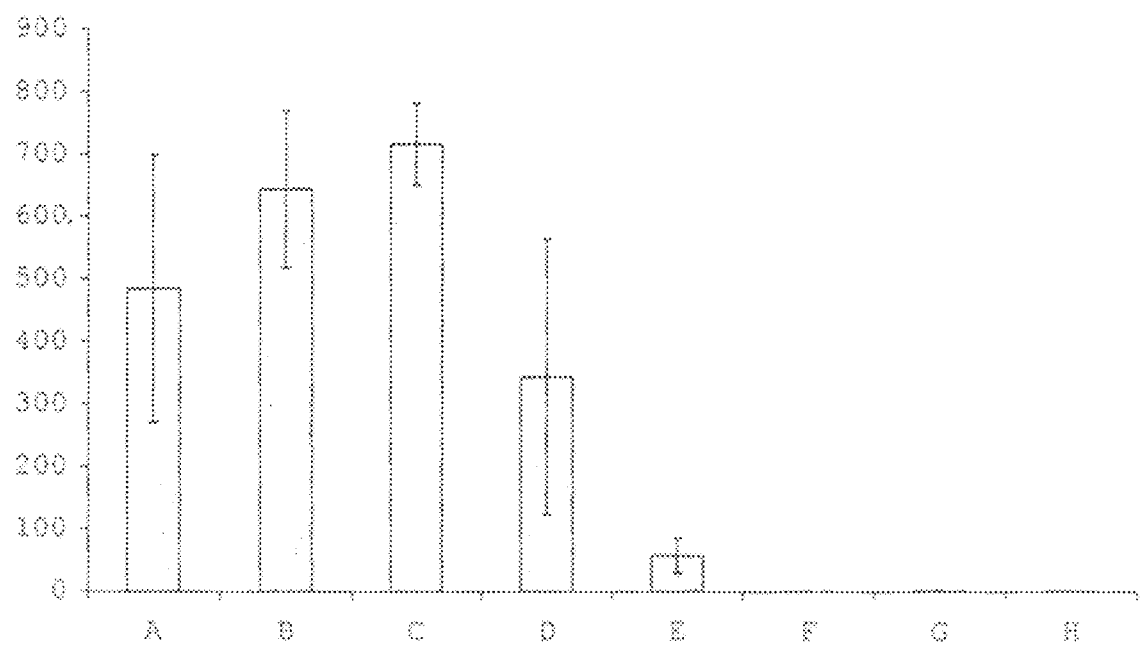
FIG. 4. Inhibition of infection of Jurkat cells by pre-incubation of X4 HIV-1$_{IIIB}$ with the carbohydrate-lipid construct designated Gb$_3$-sp3-Ad-DOPE (I) (p24 pg/mL)(r=3): A—Control; B—50 μM; C—100 μM; D—200 μM; E—400 μM; F—600 μM; G—800 μM; and H—1000 μM.

Results for triplicate experiments (r=3) are presented in Table 2 and FIG. 4.

Figure 5:
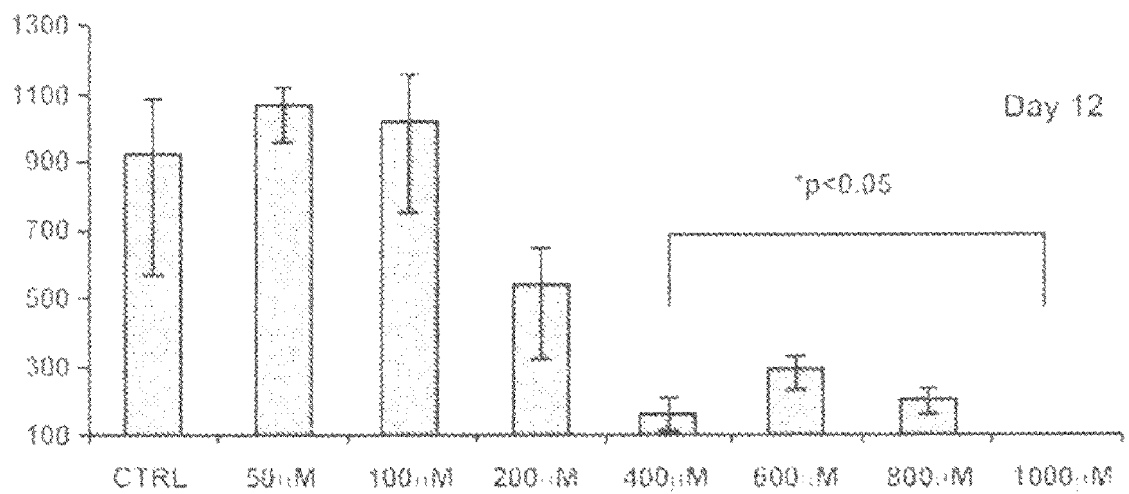
FIG. 5. Inhibition of infection of peripheral blood mononuclear cells by pre-incubation of R5 HIV-1$_{Ba-L}$ with the carbohydrate-lipid construct designated Gb$_3$-sp2-Ad-DOPE (III) (p24 pg/mL) (r=4).

Dose Response for Inhibition of Infection of Peripheral Blood Mononuclear Cells with an R5 Type Monocyte-Tropic HIV Virus HIV-1$_{Ba-L}$, an R5 type, monocyte-tropic HIV virus, was pre-incubated with Gb$_3$-sp3-Ad-DOPE (I) at the concentrations provided in FIG. 5 for 1 hour. PHA/IL-2-activated human peripheral blood mononuclear cells (PBMCs) obtained from a healthy volunteer donor were then infected by incubation with the pre-treated virus for 1 hour (n=4).

p24 antigen expression, a measure of productive HIV infection, was monitored 12 days after infection. Gb$_3$-sp3-Ad-DOPE (I) was observed to inhibit infection by HIV-1$_{Ba-L}$ at 400 μM (p<0.05) with a half-maximal inhibitory activity (IC$_{50}$) of circa 200 μM.

Dose Response for Inhibition of Infection of Jurkat C Cells with X4 HIV-1 Virus

Figure 6:
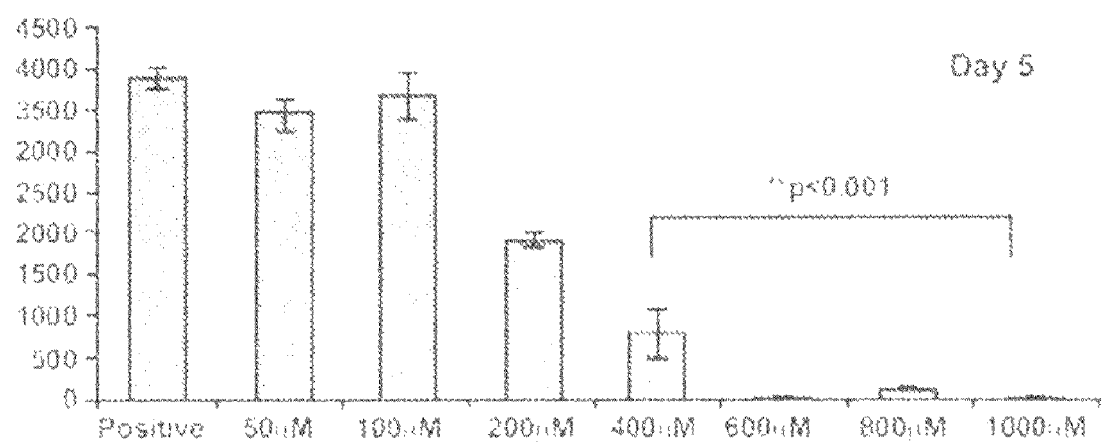
FIG. 6. Inhibition of infection of peripheral blood mononuclear cells by pre-incubation of X4 HIV-1$_{IIIB}$ with the carbohydrate-lipid construct designated Gb$_3$-sp2-Ad-DOPE (III) (p24 pg/mL) (r=4).

HIV-1$_{IIIB}$ was pre-incubated with Gb$_3$-sp3-Ad-DOPE (I) at the concentrations provided in FIG. 6 for 1 hour. Jurkat C cells were then infected by incubation with the pre-treated virus for 1 hour (n=4).

p24 antigen expression, a measure of productive HIV infection, was monitored 5 days after infection. Gb$_3$-sp3-Ad-DOPE (I) was observed to inhibit infection by HIV-1$_{IIIB}$ at 400 μM (p<0.001) with a half-maximal inhibitory activity (IC$_{50}$) of circa 200 μM.

In Vivo Studies
Mouse Model

A mouse model of HIV infection of the rectal and vaginal mucosa was used for in vivo evaluation of $Gb_3$-sp2-Ad-DOPE (III). A pseudoenvelope-typed replication-deficient VSV-G/NL4-3luc HIV-1 virus (VSV/HIV) approved for use in level 2 biocontainment was used to validate the mouse model.

Replication deficient, VSV-G enveloped HIV-1 luciferase containing recombinant virions were prepared by co-transfection of 293T cells with plasmids containing the VSV-G envelope and the HIV-1 genome lacking any and with the luciferase gene inserted into the nef gene.

10 μg of plasmid containing the envelope and 15 μg of plasmid containing the HIV genome were mixed and added drop wise to $2.5 \times 10^6$ 293T cells plated 24 hours previously. Plates were incubated for 72 hours at 37° C.

Viral supernatant was collected, centrifuged for 10 min, filtered through a 0.45 μm filter and ultracentrifuged in 8 mL aliquots over 400 μL 20% glucose for 1 hour at 19,000 rpm. Pelleted virions were resuspended in 800 μL THE buffer and stored at −80° C. until further use. Virion content was determined by p24 ELISA.

To determine infectivity of virus, $2 \times 10^5$ Jurkat C cells were plated in a 96 well tray in triplicate in 100 μL complete RPMI media lacking phenol red. 20 μL volumes of virus plus media up to a total volume of 200 μL per well was then added.

Cells were incubated for 48 hours, then lysed using Promega cell culture lysis solution. 100 μL of luciferase assay substrate was added to 20 μL of the lysed cells and luciferase activity was measured using a luminometer.

To determine if the virus infected a mouse epithelial cell line, $1 \times 10^6$ NIH3T3 cells were infected with 25 and 75 μL aliquots of virus and incubated in DMEM for 2 hours. DNA was isolated and subjected to PCR as described below.

To determine if the virus infected mouse mucosal tissue, male and female CD1 mice were challenged rectally and vaginally with 25 μL of virus administered via pipette to the rectum and vaginal cavities of euthanized mice for 2 hours. Rectal and vaginal tissue was then removed. DNA was isolated via the Qiagen DNEasy Isolation Kit for 50 mg of tissue.

Primers used for PCR amplification of HIV cDNA were forward: LTR 5'-GGGACTGGAAGGGCTAATTC-3' and reverse: L15'-AGGCAAGCTTTATTGAGGCT TAAGC-3'. Primers used for nested PCR were forward: L2 5'-CTGTG-GATCTACCACACACA AGGCTAC-3' and reverse: LTR U3 5'-CTCCCT GGAAAGTCCCCAGC-3'. Real time PCR was conducted using the Roche LightCycler 2.0 using the FastStart DNA Master Plus SYBR Green I Kit.

Figure 7:
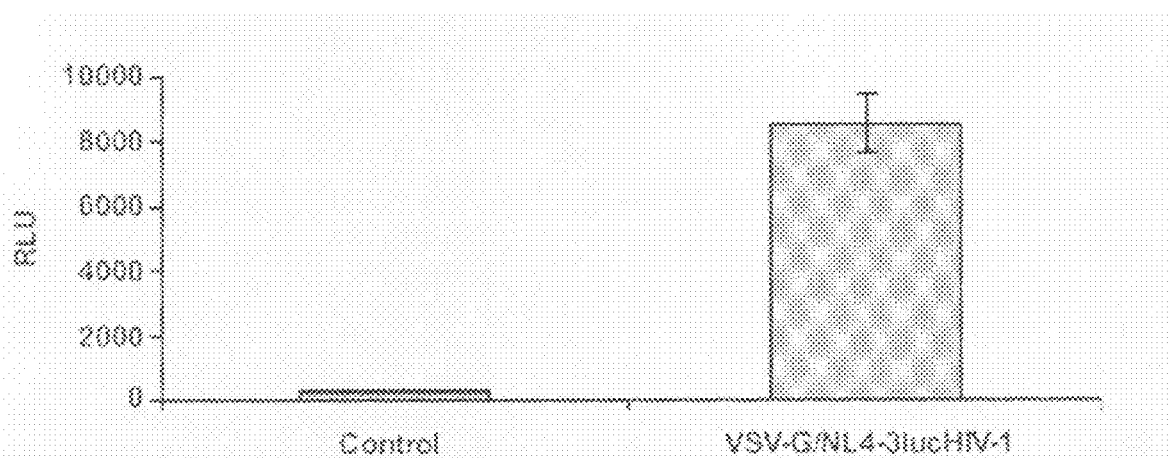
FIG. 7. Infection of Jurkat cells by pseudoenvelope-typed VSV-G/NL4-3lucHIV-1 (luciferase assay).
Figure 8:
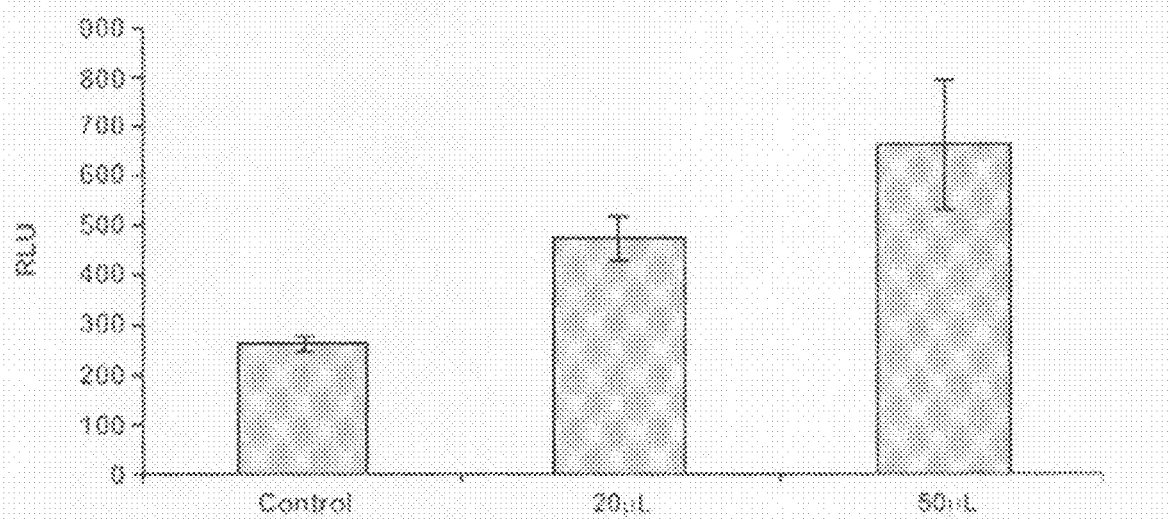
FIG. 8. Infection of NIH3T3 cells by pseudoenvelope-typed VSV-G/NL4-3lucHIV-1 (luciferase assay).
Figure 9:
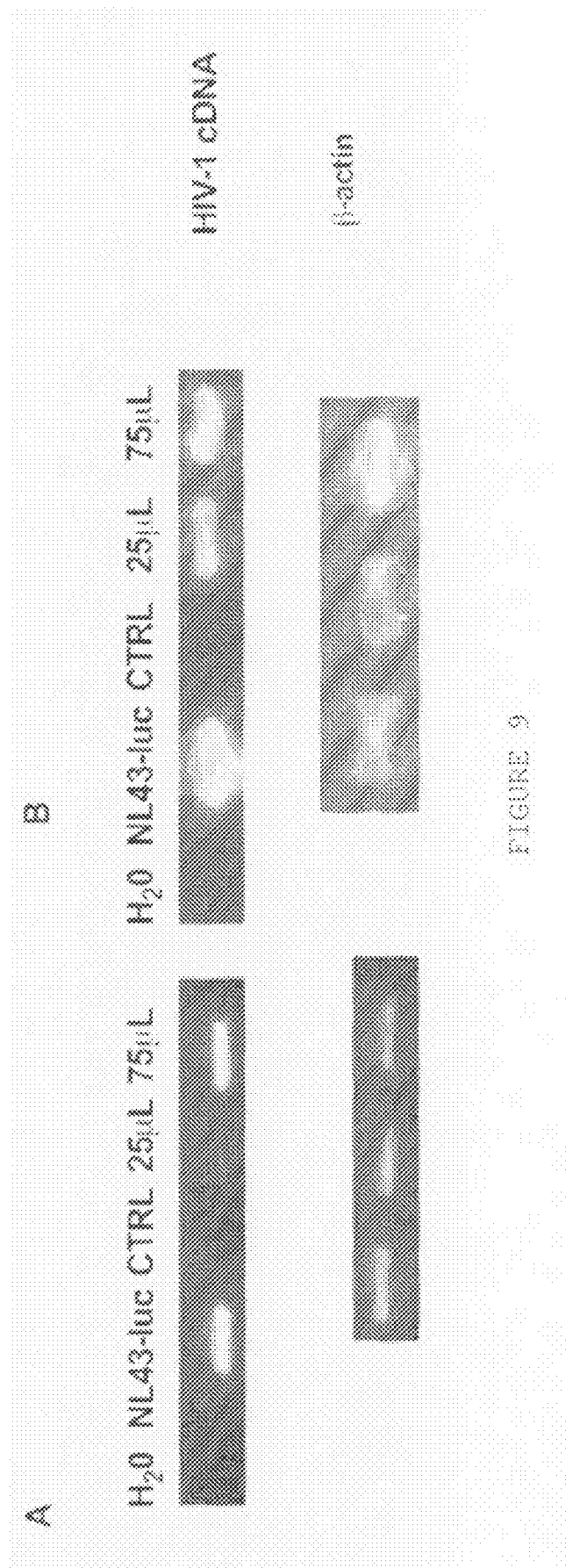
FIG. 9. Infection of (a) Jurkat cells and (b) NIH3T3 cells by pseudoenvelope-typed VSV-G/NL4-3lucHIV-1 (luciferase assay).

The pseudoenvelope-typed replication-deficient VSV-G/NL4-3luc HIV-1 virus (VSV/HIV) was demonstrated to infect both Jurkat and NIH3T3 cells by luciferase assay (FIGS. 7 and 8) and PCR (FIGS. 9a and 9b).

Figure 10:
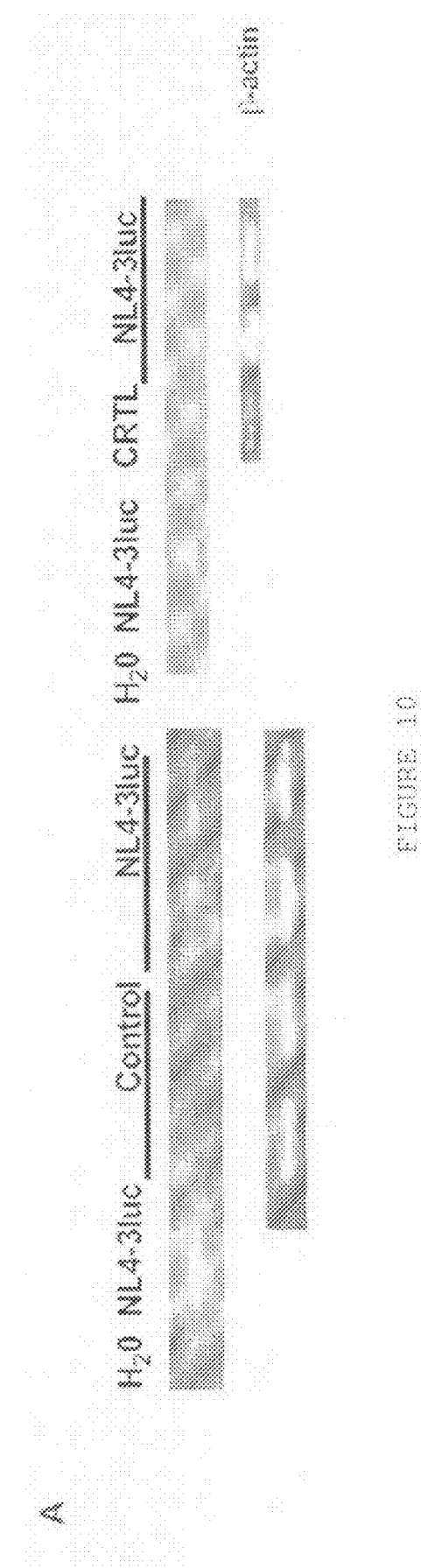
FIG. 10. Infection of (a) NIH3T3 cells and (b) Jurkat cells by pseudoenvelope-typed VSV-G/NL4-3lucHIV-1 (PCR).

The pseudoenvelope-typed replication-deficient VSV-G/NL4-3luc HIV-1 virus (VSV/HIV) was demonstrated to infect both rectal and vaginal mucosa (FIGS. 10a and 10b).

Inhibition of Rectal Infection by VSV/HIV by Gel Formulation of $Gb_3$-sp3-Ad-DOPE (III)

A preliminary trial of a carbopol-based gel was performed. A gel containing 3 mM $Gb_3$-sp2-Ad-DOPE (III) was applied to rectal mucosa of CD1 mice for 30 minutes before a one and one half hour challenge with VSV/HIV. Tissue was removed and quick frozen in liquid nitrogen. A gel containing only PBS was used as a control (n=4).

DNA was isolated from the tissue using the Qiagen tissue kit. Quantitative real time PCR (qPCR) using the Roche Lightcycler was performed to determine copy number of HIV-1 genomes using primers for the LTR region of HIV-1 and compared to a quantified HIV-1 cDNA standard curve.

Figure 11:
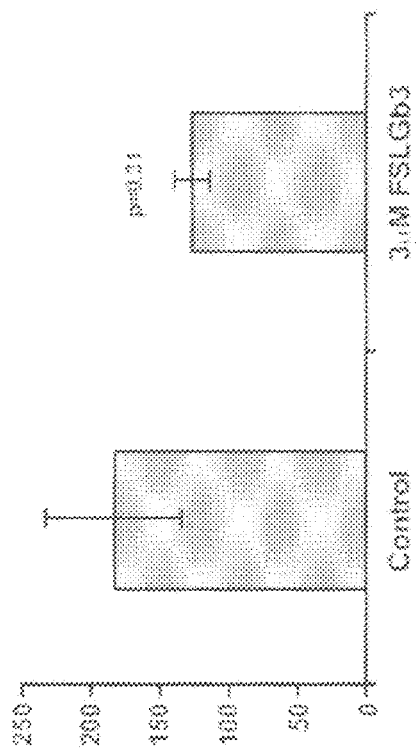
FIG. 11. Inhibition of infection of rectal mucosa by VSV/HIV by application of a carbopol-based gel containing 3 mM the carbohydrate-lipid construct designated Gb$_3$-sp2-Ad-DOPE (III) (copy number HIV-1 cDNA) (n=4).

Detection of HIV cDNA copies indicated successful viral entry and reverse transcription of the HIV genome (FIG. 11).

Inhibition of Vaginal Infection by VSV/HIV by Gel Formulation of $Gb_3$-sp2-Ad-DOPE (III)

A preliminary trial of a carbopol-based gel was performed. A gel containing 3 mM $Gb_3$-sp2-Ad-DOPE (III) was applied to vaginal mucosa of CD1 mice for 30 minutes before a one and one half hour challenge with VSV/HIV. Tissue was removed and quick frozen in liquid nitrogen. A gel containing only PBS was used as a control (n=4).

DNA was isolated from the tissue using the Qiagen tissue kit. Quantitative real time PCR (qPCR) using the Roche Lightcycler was performed to determine copy number of HIV-1 genomes using primers for the LTR region of HIV-1 and compared to a quantified HIV-1 cDNA standard curve.

Figure 12:
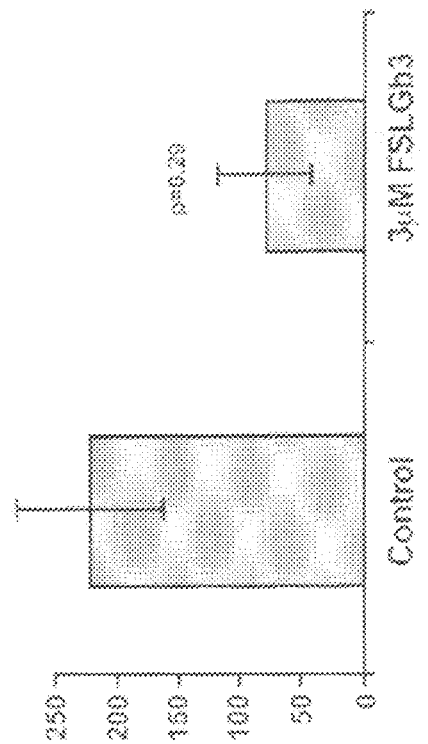
FIG. 12. Inhibition of infection of vaginal mucosa by VSV/HIV by application of a carbopol-based gel containing 3 mM the carbohydrate-lipid construct designated Gb$_3$-sp2-Ad-DOPE (III) (copy number HIV-1 cDNA) (n=4).

Detection of HIV cDNA copies indicated successful viral entry and reverse transcription of the HIV genome (FIG. 12).

Inhibition of Rectal Infection by VSV/HIV Direct Application of $Gb_3$-sp2-Ad-DOPE 3 mM $Gb_3$-sp2-Ad-DOPE (III) was applied directly to rectal mucosa of CD1 mice for 30 minutes before a one and one half hour challenge with VSV/HIV. Tissue was removed and quick frozen in liquid nitrogen (n=4).

DNA was isolated from the tissue using the Qiagen tissue kit. Quantitative real time PCR (qPCR) using the Roche Lightcycler was performed to determine copy number of HIV-1 genomes using primers for the LTR region of HIV-1 and compared to a quantified HIV-1 cDNA standard curve.

Figure 13:
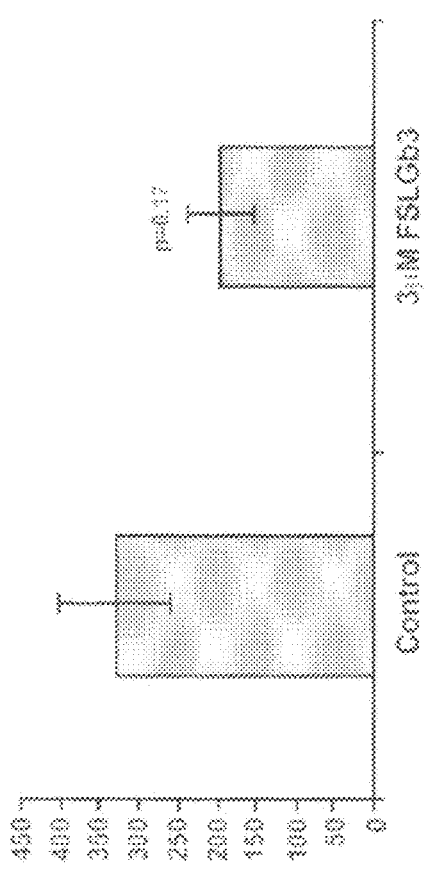
FIG. 13. Inhibition of infection of rectal mucosa by VSV/HIV by direct application of a 3 mM solution of the carbohydrate-lipid construct designated Gb$_3$-sp2-Ad-DOPE (III) (copy number HIV-1 cDNA) (n=4).

Detection of HIV cDNA copies indicated successful viral entry and reverse transcription of the HIV genome (FIG. 13).

Inhibition of Vaginal Infection by VSV/HIV Direct Application of $Gb_3$-sp2-Ad-DOPE (III)

3 mM $Gb_3$-sp2-Ad-DOPE (III) was applied directly to vaginal mucosa of CD1 mice for 30 minutes before a one and one half hour challenge with VSV/HIV. Tissue was removed and quick frozen in liquid nitrogen (n=4).

DNA was isolated from the tissue using the Qiagen tissue kit. Quantitative real time PCR (qPCR) using the Roche Lightcycler was performed to determine copy number of HIV-1 genomes using primers for the LTR region of HIV-1 and compared to a quantified HIV-1 cDNA standard curve.

Figure 14:
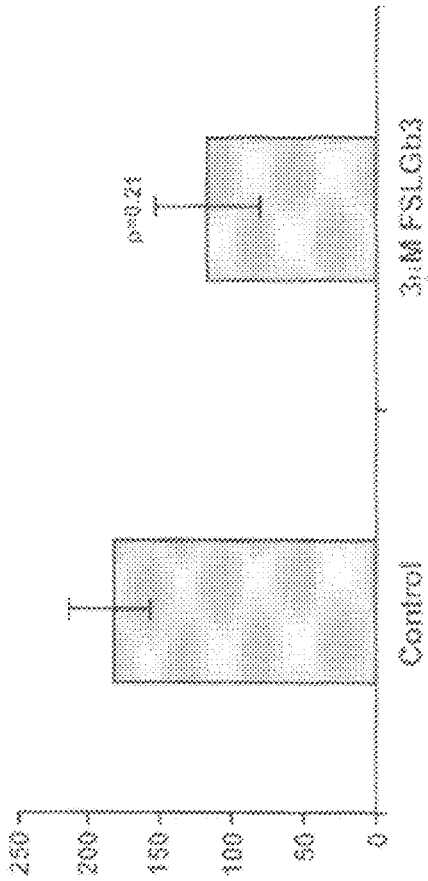
FIG. 14. Inhibition of infection of vaginal mucosa by VSV/HIV by direct application of a 3 mM solution of the carbohydrate-lipid construct designated Gb$_3$-sp2-Ad-DOPE (III) (copy number HIV-1 cDNA) (n=4).

Detection of HIV cDNA copies indicated successful viral entry and reverse transcription of the HIV genome (FIG. 14).

Although the invention has been described by way of examples indicative of its utility in the treatment of human subjects it should be appreciated that variations and modifications may be made to the claimed methods with out departing from the scope of the invention. It will be understood that for a non-specific interaction, such as the interaction between the diacyl- or dialkyl-glycerolipid portion of the carbohydrate-lipid constructs and a membrane, structural and stereoisomers of naturally occurring lipids can be functionally equivalent. Where known equivalents exist to specific features, such equivalents are incorporated as if specifically referred to in this specification. For example, it is contemplated that diacylglycerol 2-phosphate could be substituted for phosphatidate (diacylglycerol 3-phosphate) and that the absolute configuration of phosphatidate could be either R or S.

TABLE 1

Inhibition of infection of Jurkat cells by pre-incubation of
X4 HIV-1 IIIB with carbohydrate-lipid construct designated
$Gb_3$-sp3-Ad-DOPE (I) at the concentrations indicated (r = 4).

|  | control | 50 µM | 100 µM | 200 µM | 400 µM | 600 µM | 800 µM | 1000 µM |
|---|---|---|---|---|---|---|---|---|
| 1 | 52.438 | 235.054 | 200.097 | 140.632 | 89.202 | 1.008 | 1.008 | 1.209 |
| 2 | 229.629 | 220.79 | 224.205 | 14.267 | 2.213 | 1.008 | 0.205 | 1.008 |
| 3 | 50.027 | 211.147 | 237.264 | 76.345 | 83.175 | 0.205 | 3.62 | 1.611 |
| 4 | 203.513 | 47.415 | 28.531 | 221.393 | 2.816 | 0.807 | 128.578 | 0.205 |
| mean | 133.9018 | 178.6015 | 172.5243 | 113.1593 | 44.3515 | 0.757 | 33.35275 | 1.00825 |
| SD | 96.05684 | 88.00731 | 97.22216 | 88.70224 | 48.37245 | 0.380003 | 63.50024 | 0.591275 |
| SEM | 48.02842 | 44.00366 | 48.61108 | 44.35112 | 24.18623 | 0.190001 | 31.75012 | 0.295638 |

TABLE 2

Inhibition of infection of Jurkat cells by pre-incubation of
X4 HIV-1 IIIB with carbohydrate-lipid construct designated
$Gb_3$-sp3-Ad-DOPE (I) at the concentrations indicated (r = 3).

|  | control | 50 µM | 100 µM | 200 µM | 400 µM | 600 µM | 800 µM | 1000 µM |
|---|---|---|---|---|---|---|---|---|
| 1 | 52.438 | 235.054 | 200.097 | 140.632 | 2.213 | 1.008 | 1.008 | 1.209 |
| 2 | 229.629 | 220.79 | 224.205 | 76.345 | 83.175 | 1.008 | 0.205 | 1.008 |
| 3 | 203.513 | 211.147 | 237.264 | 221.393 | 2.816 | 0.807 | 3.62 | 0.205 |
| mean | 161.86 | 222.3303 | 220.522 | 146.1233 | 29.40133 | 0.941 | 1.611 | 0.807333 |
| SD | 95.65768 | 12.0277 | 18.85523 | 72.67975 | 46.57034 | 0.116047 | 1.785571 | 0.531229 |
| SEM | 55.22799 | 6.944197 | 10.88607 | 41.96168 | 26.8874 | 0.067 | 1.0309 | 0.306705 |

REFERENCES

Asher et al (2005) *The erythrocyte viral trap: Transgenic expression of viral receptor on erythrocytes attenuates coxsackievirus B infection*, PNAS, 102:36, 12897-12902

Bhat et al (1993) *The Galactosyl Ceramide/Sulfatide Receptor Binding Region of HIV-lgp120 Maps to Amino Acids 206-275*, Aids Res Human Retrovirus, 9:175-181

Santini et al (1998) *Sulfatide Inhibits HIV-1 Entry Into CD4−/CXCR4+ Cells*, Virology 246:211-220

Lund et al (2006) *A Novel Soluble Mimic Of The Glycolipid, Globotriaosyl Ceramide Inhibits HIV Infection*, AIDS, 20:333-343

Mahfoud et al (2002) *A Novel Soluble Analog of the HIV-1 Fusion Cofactor, Globotriaosylceramide ($Gb_3$), eliminates the cholesterol requirement for high affinity gp120/$Gb_3$ Interaction*, J Lipid Res, 43:1670-1679

Mylvaganam and Lingwood (1999a) *Adamantyl Globotriaosyl Ceramide: A Monovalent Soluble Mimic Which Inhibits Verotoxin Binding to Its Glycolipid Receptor*, Biochemical and Biophysical Research Communications, 257:391-394

Mylvaganam and Lingwood (1999b) *A Convenient Oxidation of Natural Glycosphingolipids to Their "Ceramide Acids" for Neo-Glycoconjugation: Bovine Serum Albumin-Glycoceramide Acid Conjugates as Investigative Probes for HIV gp120 Coat Protein Glycosphingolipid Interactions*, J Biol Chem, 274:20725-20732

Nehete et al (2002) *A Post-CD4-Binding Step Involving Interaction of the V3 Region of Viral gp120 with Host Cell Surface Glycosphingolipids is Common to Entry and Infection by Diverse HIV-1 Strains*, Antiviral Res, 56:233-251

Neri et al (2007) *Monovalent Gb3−/Gb2-Derivatives Conjugated with a Phosphatidyl Residue: A Novel Class of Shiga Toxin-Neutralizing Agent*, Biol Pharm Bull, 30(9), 1697-1701

Sun et al (2006) Tetrahedron Letters, 47:7371-7374

Schengrund (2003) *"Multivalent" saccharides: development of new approaches for inhibiting the effects of glycosphingolipid-binding pathogens*, Biochem Pharmacol, 65(5), 699-707

Fantini et al (1993) *Infection of colonic epithelial cell lines by type 1 human immunodeficiency virus is associated with cell surface expression of galactosylceramide, a potential alternative gp120 receptor*, PNAS, 90:7, 2700-2704.

Hanada (2005) *Sphingolipids in Infectious Diseases*, Japanese Journal of Infectious Diseases, 58:3, 131-148

Karlsson (1995) *Microbial recognition of target-cell glycoconjugates*, Current Opinion in Structural Biology, 5:5, 622-635

Isa et al (1997) *Functional and structural analysis of the sialic acid-binding domain of rotaviruses*, Journal of Virology, 71:9, 6749-6756

Matrosovicha et al (1997) *Avian Influenza A Viruses Differ from Human Viruses by Recognition of Sialyloligosaccharides and Gangliosides and by a Higher Conservation of the HA Receptor-Binding Site*, Virology, 233:1, 224-234

Miller-Podraza et al (2000) *A strain of human influenza A virus binds to extended but not short gangliosides as assayed by thin-layer chromatography overlay*, Glycobiology, 10:10, 975-982

Suzuki (1994) *Gangliosides as influenza virus receptors. Variation of influenza viruses and their recognition of the receptor sialo-sugar chains*, Progress in Lipid Research, 33:4: 429-457.

Connor et al (1994) *Receptor specificity in human, avian, and equine H2 and H3 influenza virus isolates*, Virology, 205, 17-23.

Matrosovich et al (1999) *The Surface Glycoproteins of H5 Influenza Viruses Isolated from Humans, Chickens, and Wild Aquatic Birds Have Distinguishable Properties*, Journal of Virology, 73:2, 1146-1155

Willoughby et al (1990) *Rotaviruses specifically bind to the neutral glycosphingolipid asialo-GM1*, Journal of Virology, 64:10, 4830-5

The invention claimed is:

1. A method of inhibiting infection of the cells by human immunodeficiency virus comprising topically administering to a subject at risk of infection by human immunodeficiency virus a construct of the formula F-S1-S2-L where F is 1-O—(O-α-D-galactopyranosyl-(1→4)-O-β-D-galactopyranosyl-(1→4)-β-D-glucopyranosyl, S1 is 2-aminoethyl, 3-aminopropyl, 4-aminobutyl or 5-aminopentyl, S2 is —CO(CH$_2$)$_3$CO—, —CO(CH$_2$)$_4$CO or —CO(CH$_2$)$_5$CO—, and L is a diacyl- or dialkyl glycerophospholipid.

2. The method of claim 1 where the topical administration is as a cream or suppository.

3. A method of promoting clearance of human immunodeficiency virus from an infected subject comprising intravascularly administering to the subject a construct of the formula FS1-S2-L where F is 1-O—(O-α-D-galactopyranosyl-(1→4)-O-β-Dgalactopyranosyl-(1→4)-β-D-glucopyranosyl, S1 is 2-aminoethyl, 3-aminopropyl, 4-aminobutyl or 5-aminopentyl, S2 is —CO(CH$_2$)$_3$CO—, —CO(CH$_2$)$_4$CO— or —CO(CH$_2$)$_5$CO—, and L is a diacyl- or dialkyl-glycerophospholipid.

4. The method of claim 3 where the administration is by intravenous injection.

5. The method of claim 1 where L is phosphatidylethanolamine.

6. The method of claim 3 where L is phosphatidylethanolamine.

7. The method of claim 1 where L is derived from one or more cis-desaturated fatty acids.

8. The method of claim 3 where L is derived from one or more cis-desaturated fatty acids.

9. The method of claim 7 where L is 1,2-O-dioleoyl-sn-glycero-3-phosphatidylethanolamine.

10. The method of claim 8 where L is 1,2-O-dioleoyl-sn-glycero-3-phosphatidylethanolamine.

* * * * *